United States Patent [19]

Kuroda et al.

[11] Patent Number: 5,744,307
[45] Date of Patent: Apr. 28, 1998

[54] METHOD FOR MEASURING ADENYL GROUP-CONTAINING SUSBSTANCES

[75] Inventors: Naotaka Kuroda; Kenichiro Nakashima; Shuzo Akiyama, all of Nagasaki; Kamon Shirakawa, Saitama; Naofumi Sato, Saitama; Toshinori Kanamori, Saitama, all of Japan

[73] Assignee: Mochida Pharmaceutical Co., Ltd., Tokyo, Japan

[21] Appl. No.: 527,097

[22] Filed: Sep. 12, 1995

Related U.S. Application Data

[63] Continuation of Ser. No. 109,721, Aug. 19, 1993, abandoned.

[30] Foreign Application Priority Data

Feb. 26, 1993 [JP] Japan .................................. 5-062631
Mar. 26, 1993 [JP] Japan .................................. 5-067906

[51] Int. Cl.⁶ ........................................ C12Q 1/68
[52] U.S. Cl. .................. 435/6; 435/7.1; 435/810; 436/501; 536/25.3; 935/77; 935/78
[58] Field of Search .................. 435/6, 7.1, 810; 436/501; 536/23.1, 24.1, 24.3–24.33, 25.3; 935/77, 78

[56] References Cited

U.S. PATENT DOCUMENTS 4,828,979 5/1989 Klevan et al. ..................... 435/6

*Primary Examiner*—Ardin H. Marschel
*Attorney, Agent, or Firm*—Birch, Stewart, Kolasch & Birch, LLP

[57] ABSTRACT

A method for the measurement of adenyl group-containing substances which comprises deriving a chemiluminescent substance by allowing a compound to react with adenyl group in a substance to be measured, and qualitatively or quantitatively measuring the substance to be measured using a luminescent intensity obtained from the chemiluminescent substance as a marker.

24 Claims, 18 Drawing Sheets

METHOD FOR MEASURING ADENYL GROUP-CONTAINING SUSBSTANCES

This application is a continuation of application Ser. No. 08/109,721 filed on Aug. 19, 1993, now abandoned.

FIELD OF THE INVENTION

This invention relates to a method for the measurement of adenyl group-containing substances. More particularly, it relates to a method in which adenyl group in a substance to be measured is chemically modified and the substance is measured qualitatively or quantitatively using chemiluminescent activity of the modified substance as a marker.

BACKGROUND OF THE INVENTION

Adenine, adenosine, adenosine phosphate compounds, DNA, RNA and the like are known as adenyl group-containing substances which take important roles a living body as composing elements of coenzymes, high-energy phosphate compounds, genes and the like.

In general, measurement of adenine and adenosine is carried out with the aid of complicated high performance liquid chromatography (HPLC), because they cannot be separated for the measurement from other nucleic acid bases such as guanine, guanosine and the like without employing chromatographic separation techniques.

On the other hand, measurement of nucleic acids is carried out generally making use of their ultraviolet absorption at 260 nm, but such a method has problems with regard to its measuring sensitivity and specificity. In recent years, an ethidium bromide-aided fluorochrome technique has been developed. This technique, however, can hardly be used for accurate quantitative determination of nucleic acids because the fluorescent intensity fluctuates extensively depending on the difference in three-dimensional structures of nucleic acids. In addition, it requires special treatment in handling because ethidium bromide is a strong carcinogenic substance.

It is accordingly an object of the present invention to measure adenyl group-containing substances by simple means with high specificity and sensitivity.

SUMMARY OF THE INVENTION

The inventors of the present invention have found a new measuring method in which a chemiluminescent substance is derived by allowing a compound (reactable with adenyl group) represented by the following general formula 1 to react with the adenyl group in a substance to be measured, and the adenyl group-containing substance is measured qualitatively or quantitatively with a high sensitivity based on the luminescent intensity obtained from the luminescent substance. The present invention has been accomplished on the basis of this finding.

Accordingly, the present invention provides a method for the measurement of adenyl group-containing substances which comprises deriving a chemiluminescent substance by allowing a compound represented by the following general formula 1 to react with the adenyl group in a substance to be measured, and qualitatively or quantitatively measuring the substance to be measured using a luminescent intensity obtained from the chemiluminescent substance as a marker:

$$R^1-CO-R^2 \quad (1)$$

wherein $R^1$ is a hydrogen atom; an alkyl group, an alkenyl group or an alkinyl group having 1 to 12 carbon atom(s); an aryl group or an aromatic heterocyclic group having 1 to 18 carbon atom(s), where the $R^1$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group; and a heterocyclic group, and the group itself which substitutes or ring-condenses the $R^1$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group; and a heterocyclic group, $R^2$ is an aldehyde group or a group represented by —CH$(XR^3)(X'R^4)$ in which X and X' may be the same or different group and are selected from oxygen atom, sulfoxide group, sulfone group, sulfur atom, selenoxide group and selenium atom, and $R^3$ and $R^4$ may be the same or different groups which may form a ring by their partial binding and are selected from hydrogen atom; an alkyl group, an alkenyl group or an alkinyl group having 1 to 12 carbon atom(s); and an aryl group having 1 to 18 carbon atom(s), wherein the $R^3$ and $R^4$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkyl amino group, an alkyl group, an alkenyl group, an alkinyl group or an alkoxy group having 1 to 12 carbon atom(s); a polyalkoxy group; an aryl group; an aryloxy group; and a heterocyclic group, and the group itself which substitutes or ring-condenses the $R^3$ and $R^4$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group; and a heterocyclic group.

Another object of the present invention is to provide the just described method for the measurement of adenyl group-containing substances wherein the substance to be measured is adenine, adenosine, an adenosine phosphate compound, DNA or RNA.

Still another object of the present invention is to provide a method for the measurement of adenyl group-containing substances which comprises measuring luminescent intensity of the aforementioned chemiluminescent substance by adding a reaction initiator to the reaction solution in the presence of dimethylformamide, isopropanol, acetonitrile, dioxane, dimethyl sulfoxide or water as a solvent for luminescence.

A further object of the present invention is to provide the measuring method which comprises deriving a chemiluminescent substance by allowing a compound of the aforementioned general formula 1 to react with adenyl groups in the target nucleic acid or an amplified product thereof, and qualitatively or quantitatively measuring the target nucleic acid using a luminescent intensity obtained from the chemiluminescent substance as a marker in the case of a DNA probe method for the measurement of adenyl group-containing substances in which a target nucleic acid in a test sample is detected using a capture probe capable of undergoing complementary binding to the target nucleic acid.

Still further object of the present invention is to provide the measuring method which comprises deriving a chemiluminescent substance by allowing the aforementioned compound to react with adenyl groups in the target nucleic acid or an amplified product thereof, and qualitatively or quantitatively measuring the target nucleic acid using a luminescent intensity obtained from the chemiluminescent substance as a marker in the case of a target nucleic acid measuring method for the measurement of adenyl group-containing substances in which a target nucleic acid in a test sample is detected by amplifying it by an enzyme-aided nucleic acid amplification technique.

Other objects and advantages of the present invention will be made apparent as the description progresses.

DETAILED DESCRIPTION OF THE INVENTION

Figure 1:
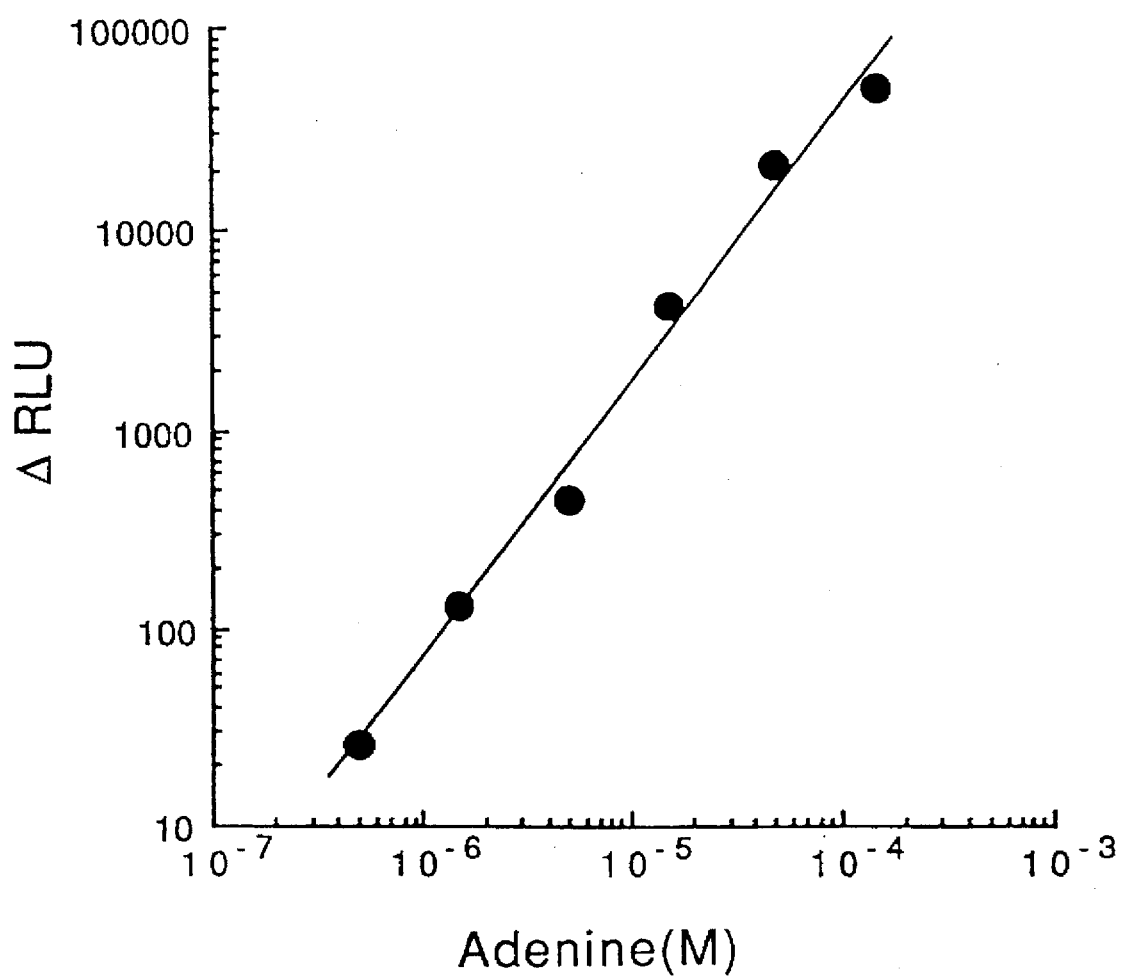
FIG. 1 is a graph showing a calibration curve of adenine when phenylglyoxal dimetylacetal is used.

The method of the present invention is used for the measurement of samples (test sample) which contain substances to be measured. Examples of such samples include blood body fluid, urine, tissues, microbial culture broths and extracts thereof, as well as amplified products of nucleic acids contained therein prepared by polymerase chain reaction (PCR) and the like techniques.

The substances to be measured (to be tested) by the measuring method of the present invention are adenyl group-containing substances, and typical examples of such substances include adenine, adenosine, adenosine phosphate compounds, DNA, RNA and the like. The inventive method can be applied also to the measurement of adenyl group-containing artificially modified nucleic acids.

The compound to be used in the measuring method of the present invention is a substance represented by the following general formula 1 in which $R^1$ and $R^2$ are selected from the following substituent groups:

$$R^1\text{—CO—}R^2 \tag{1}$$

wherein $R^1$ is hydrogen atom; an alkyl group, an alkenyl group or an alkinyl group having 1 to 12 carbon atom(s); an aryl group or an aromatic heterocyclic group having 1 to 18 carbon atom(s), where said $R^1$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group; and a heterocyclic group, and the group itself which substitutes or ring-condenses said $R^1$ may be substituted or ring-condensed with at least one group selected from the class consisting of carboxy group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atoms; a polyalkoxy group; an aryl group; an aryloxy group; and a heterocyclic group, $R^2$ is aldehyde group or a group represented by —CH(XR$^3$)(X'R$^4$), X and X' may be the same or different groups and are selected from oxygen atom, sulfoxide group, sulfone group, sulfur atom, selenoxide group and selenium atom, and $R^3$ and $R^4$ are the same or different groups which may form a ring by their partial binding and are selected from hydrogen atom; an alkyl group, an alkenyl group or an alkinyl group having 1 to 12 carbon atom(s); and an aryl group having 1to 18 carbon atom(s), where said $R^3$ and $R^4$ may be substituted or ring-condensed with at least one group selected from the class consisting of carboxyl group; hydroxyl group; amino group; amide group; sulfonamide group; sulfide group, sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group; and a heterocyclic group, and the group itself which substitutes or ring-condenses said $R^3$ and $R^4$ may be substituted or ring-condensed with at least one group selected from the class consisting of carboxyl group; hydroxyl group; amino group; amide group; sulfonamide group; sulfide group; sulfoxide group; sulfone group; nitro group; a halide atom; mercapto group; carbonyl group; azide group; an alkylamino group, an alkyl group, an alkenyl group, an alkinyl group or an alkoxy group having 1 to 12 carbon atom(s); a polyalkoxy group; an aryl group; an aryloxy group;

and a heterocyclic group.

In the above formula, $R^1$ is a group which exerts an influence upon the resonance structure of the luminescent substance to be derived and can be selected from the aforementioned substituent groups.

Preferably, the $R^1$ in the general formula 1 may be a phenyl group or an alkyl group having 1 to 12 carbon atoms.

A first group which substitutes or ring-condenses the $R^1$ group and a second group which substitutes or ring-condenses the first group have the same definition as defined in the above formula 1.

$R^2$ is a group which binds directly to the adenyl group and is an aldehyde group or a group represented by —CH(XR$^3$)(X'R$^4$) in which X, X', R$^3$ and R$^4$ may be selected from the aforementioned substituent groups.

Especially, the group represented by —CH(XR$^3$)(X'R$^4$) is preferable because of low blank value. In that case, its X, X', R$^3$ and R$^4$ have the same definition as defined in the general formula 1.

Preferred examples of the compounds include phenylglyoxal (referred to as "PG" hereinafter), methylglyoxal (referred to as "MG" hereinafter), methylglyoxal dimethylacetal (referred to as "MGA" hereinafter), ethylglyoxal dimethylacetal (referred to as "EGA" hereinafter), and n-butylglyoxal dimethylacetal (referred to as "BuGA" hereinafter).

In addition, an acetal or the like derivative provided from the compound of the inventive method and an alcohol derivative in the presence of an acid catalyst is also included in the compound of the present invention, because, when such a derivative itself is used as a compound in the measuring method of the present invention, it undergoes substantially the same reaction and gives a chemiluminescent substance as the result.

In the practice of the measuring method of the present invention, a chemiluminescent substance is firstly derived by allowing the compound to react with a substance to be measured.

As a solvent to be used in this reaction, generally used polar solvents can be used, particularly isopropanol (referred to as "i-PrOH" hereinafter), ethanol or dimethyl sulfoxide (referred to as "DMSO" hereinafter) is preferred. Also, this reaction may be carried out preferably under an acidic condition using an acid catalyst which is more preferably hydrochloric acid or perchloric acid.

The reaction may be carried out preferably at a temperature of higher than ordinary temperature, more preferably at 70° to 100° C. for the purpose of completing the reaction quickly.

Next, a luminescent reaction is carried out by adding a luminescent solvent and following a reaction initiator optionally with surface-active agent to the chemiluminescent substance from the above reaction in order to emit chemiluminescence, and the luminescent intensity of the resulting chemiluminescent substrate is measured. In this instance, a surface active agent may be added optionally to the reaction initiator.

Generally used polar solvents such as i-PrOH, dimethylformamide (referred to as "DMF" hereinafter), dioxane, acetonitrile, diglyme, DMSO, water and the like may be used as the solvent for luminescence, of which i-PrOH, DMF, acetonitrile, dioxane, DMSO and/or water are(is) particularly preferred.

An oxidizing agent such as $H_2O_2$ or the like may or may not be used in the measuring method of the present invention though, in general, such an agent is necessary for the luminescence reaction of chemiluminescent substances.

For example, it is desirable to add $H_2O_2$ when PG is used. The addition amount of $H_2O_2$ is preferable in the concentration of from 10 to 100 mM. In the case of a concentration of the oxidizing agent if smaller than 10 mM, it would cause decrease of the luminescent intensity, and if that of the agent is larger than 100 mM, it would entail increased background.

When DMF for HPLC grade (peroxide max 0.001% (as $H_2O_2$)) was used as a solvent for luminescent and a PG-aided measurement was carried out by adding DMF with and without 50 mM of $H_2O_2$, reduction of the intensity of luminescence and decrease in the signal noise ratio (S/N ratio) were found in the latter case.

Contrary to the case of PG, when $R^1$ is an alkyl group, in the case of no addition of 50 mM $H_2O_2$ the S/N ratio increases in comparison with the case of the addition of 50 mM $H_{2O2}$. Such a difference seems to occur due to markedly high oxidation sensitivity of the chemiluminescent substance produced by the reaction of the measured substance with the compound, which is a newly found characteristic feature. As long as a commonly used solvent reagent is used as the luminescent solvent, addition of $H_2O_2$ as an oxidizing agent is not necessary, which is advantageous from the view point of simple reagent preparation and low operation cost.

Furthermore, an SH agent (sulfhydryl reagent) can be added. It is desirable to add 2-mercaptoethanol (2-ME) as an SH agent in an approximate amount of from 3 to 20 mM, because prolongation of the chemiluminescent emission and increase in the chemiluminescent intensity can be obtained, as well as decrease in background.

As an initiator of the chemiluminescence, NaOH is preferable.

Also, additives such as a surface active agent and the like may be added for the purpose of controlling chemiluminescent emission, luminescent intensity and the like.

Detection of luminescence may be effected by the use of a photon counter, X-ray films and the like, of which a photon counter is preferable because quantitative measurement can be made.

Being specific for adenyl group, the method of the present invention hardly undergo influence of nucleic acid bases and derivatives thereof, such as thymine, cytosine, guanine, uracil and the like.

$N^6$ methylated adenine which is an adenine derivative and is in natural, is not detected as it is.

Such a high specificity of the method of the present invention can be used efficiently in a DNA probe method in which a target nucleic acid is hybridized with a capture probe containing a sequence complementary to the target nucleic acid, thereby the target nucleic acid is detected in sequence specific manner.

That is, only the target nucleic acid-originated adenyl group in a test sample can be detected when a capture probe which does not derive a chemiluminescent substance by its reaction with a compound is prepared by 1) designing a capture probe which does not contain adenyl group, 2) deleting adenyl group-corresponding portion of bases from a capture probe or 3) modifying or substituting adenyl group in a capture probe into or with a nonreactive group described above, and its reaction product derived by reacting the capture probe with the test sample is measured by the method of the present invention. The target nucleic acid-originated adenyl group is also able to be measured using an adenyl group-containing capture probe as it is, by subtracting the capture probe-originated luminescent intensity from the detected luminescent intensity.

A compound represented by the aforementioned formula 1 is used in this type of method as a compound.

While prior art DNA probe techniques require complex handling because a target nucleic acid bound to a capture probe must be further reacted with a labeled probe or a labeled antibody, the DNA probe-aided measuring method of the present invention is an unconventionally simple and useful method because it can measure a capture probe-bound target nucleic acid directly without using a labeled substance.

For example, a capture probe whose adenine portion is substituted with a cross linking reagent such as Uni-Link™ AminoModifier (Clontech Laboratories, Inc.) is prepared using a DNA synthesizer and immobilized on an amino group-introduced microtiter plate using glutaraldehyde. Thereafter, a target nucleic acid is detected by adding a test sample to the resulting plate to effect the reaction, washing the plate and then measuring the target nucleic acid by the measuring method of the present invention.

The measuring method of the present invention is also useful to apply to a target nucleic acid measuring method in which a target nucleic acid in a test sample is amplified by an enzyme-aided nucleic acid amplification method such as PCR method, and both or either of the target nucleic acid and its amplified product in the resulting reaction solution is measured.

That is, a DNA fragment which has been designed to exclude adenyl groups or inactivated by deletion, modification or substitution of adenyl groups, for the purpose of preventing from deriving a chemiluminescent substance same as the case of the aforementioned capture probe, is used as an amplification primer of a target nucleic acid. After amplifying the target nucleic acid by PCR using the amplification primer to which a specific binding substance, such as biotin, antigen and the like has been chemically bound (this substance is also designed or modified to prevent from deriving an adenyl group based chemiluminescent substance in the same manner as the case of the amplification primer), the specific binding substance in the resulting reaction solution is allowed to react with a solid phase on which avidin, streptavidin, antibody and the like substance to be bound with the specific binding substance has been immobilized. After washing the solid phase, measurement is carried out by the aforementioned method using a compound represented by the aforementioned formula 1 as a compound. Since excess primers do not produce luminescence in the measuring system, the luminescence originated from the PCR amplification product of the target nucleic acid can be detected selectively without requiring a step for the separation of the amplified product and primers in the reaction solution by electrophoresis and the like technique after the amplification reaction.

Also, it is possible to introduce a specific binding substance into a PCR amplification product by the use of triphosphate of a nucleotide other than an adenosine labeled with a specific binding substance such as biotin, antigen and the like. When PCR is carried out in the above method, the luminescence originated solely from the PCR amplification product of the target nucleic acid is detected, because excess primers and adenosine triphosphate do not bind to a substance expected (avidin and the like) to which a specific binding substance is bound.

In addition to the method mentioned above, it is able to apply a method in which an amplified PCR product is discovered solely by using an ultrafiltration membrane, and a method by using a resin carrier capable of binding specifically to only the amplified PCR product.

With the advance of nucleic acid amplification techniques including the recently developed PCR method, importance of the determination of amplified nucleic acids has been increasing broadly from the fundamental research in biochemistry to the clinical application in medical science. The measuring method of the present invention can measure such amplified nucleic acids easily and simply within a short time, and, since the measured values depend on the amount of adenyl groups, the inventive method does not undergo influence of the differences in three-dimensional structures of nucleic acids.

The measuring method of the present invention can be applied to other methods than the detection of nucleic acids.

That is, the amount of a substance to be tested contained in the test sample can be measured with the chemiluminescence in the same manner as the case of the above nucleic acids, by using an adenine polymer as a marker substance of antibody or antigen in an immunoassay method in which a substance to be tested in a test sample is detected making use of the immunological reaction of the substance to be tested. Also, when a nucleic acid is used as a marker substance, the amount of a substance to be tested can be calculated by amplifying the nucleic acid by PCR and measuring the resulting PCR amplification product with the chemiluminescence.

For example, qualitative or quantitative measurement of a substance to be measured can be achieved by deriving a chemiluminescent substance by allowing a compound represented by the aforementioned formula 1 to react with adenyl groups in an amplified product, and qualitatively or quantitatively measuring the substance to be measured using a luminescent intensity obtained from the chemiluminescent substance as a marker, wherein said amplified product is obtained by an enzyme-aided nucleic acid amplification technique using a nucleic acid moiety of an antibody labeled with an adenyl group-containing substance, a nucleic acid or a mixture thereof as a target nucleic acid, or using a nucleic acid moiety of an antigen labeled with an adenyl group-containing substance, a nucleic acid or a mixture thereof as a target nucleic acid.

EXAMPLES

The following examples are provided to further illustrate the present invention. It is to be understood, however, that the examples are for purpose of illustration only and are not to be construed to limit the scope of the invention.

(Example 1)

Calibration curve of adenine using phenylglyoxal

Adenine was dissolved in a small amount of distilled water and made into serial dilutions of 0 to $1.5 \times 10^{-4}$M with i-PrOH. A 100 µl portion of each sample solution having respective adenine concentration was put in a glass vial, followed by the addition of 50 µl of each of 0.4M PG and 1.2M hydrochloric acid dissolved in i-PrOH, and the vial was then sealed and heated at 100° C. for 2 hours. The thus obtained reaction solution was cooled and used for the measurement of chemiluminescence in the following manner. A 20 µl portion of the reaction solution was put in a sample tube for measurement and mixed with 400 µl of DMF containing 50 mM of hydrogen peroxide and 5 mM of 2-ME. After arranging the sample tube in LUMIPHOTOM-ETER TD400 (LABO SCIENCE), 100 μl of 0.15M sodium hydroxide aqueous solution was added to the tube to start the luminescent reaction, and the resulting luminescent intensity was measured for 1 minute just after the addition of the alkaline solution.

When a calibration curve of adenine was prepared from the thus obtained luminescent intensity, a satisfactorily straight line was obtained within the range of from $5 \times 10^{-7}$M to $1.5 \times 10^{-4}$M as shown in FIG. 1. In the FIG. 1, the axis of abscissa indicates adenine concentration, and the axis of ordinate indicates a value obtained by subtracting the luminescent intensity of blank (no addition of adenine) from the luminescent intensity of each adenine solution having respective concentration.

(Example 2)

Calibration curve of adenine using methylglyoxal dimethylacetal

Adenine was dissolved in a small amount of distilled water and made into serial dilutions of 0 to $5 \times 10^{-4}$M with i-PrOH. A 100 μl portion of each sample solution having respective adenine concentration was put in a glass vial, followed by the addition of 50 μl of 0.3M MGA and the same volume of 1.2M hydrochloric acid dissolved in i-PrOH, and the vial was then sealed and heated at 100° C. for 2 hours. The thus obtained reaction solution was cooled and used for the measurement of chemiluminescence in the following manner. A 20 μl portion of the reaction solution was put in a glass tube for measurement and mixed with 400 μl of DMF containing 5 mM of 2-ME. After arranging the glass tube in a chemiluminescence analyzer (LB952T/16, Berthold), 300 μl of 0.25M sodium hydroxide aqueous solution was added to the tube to start the luminescent reaction, and the resulting luminescent intensity was measured for 2 seconds just after the addition of the alkaline solution.

Figure 2:
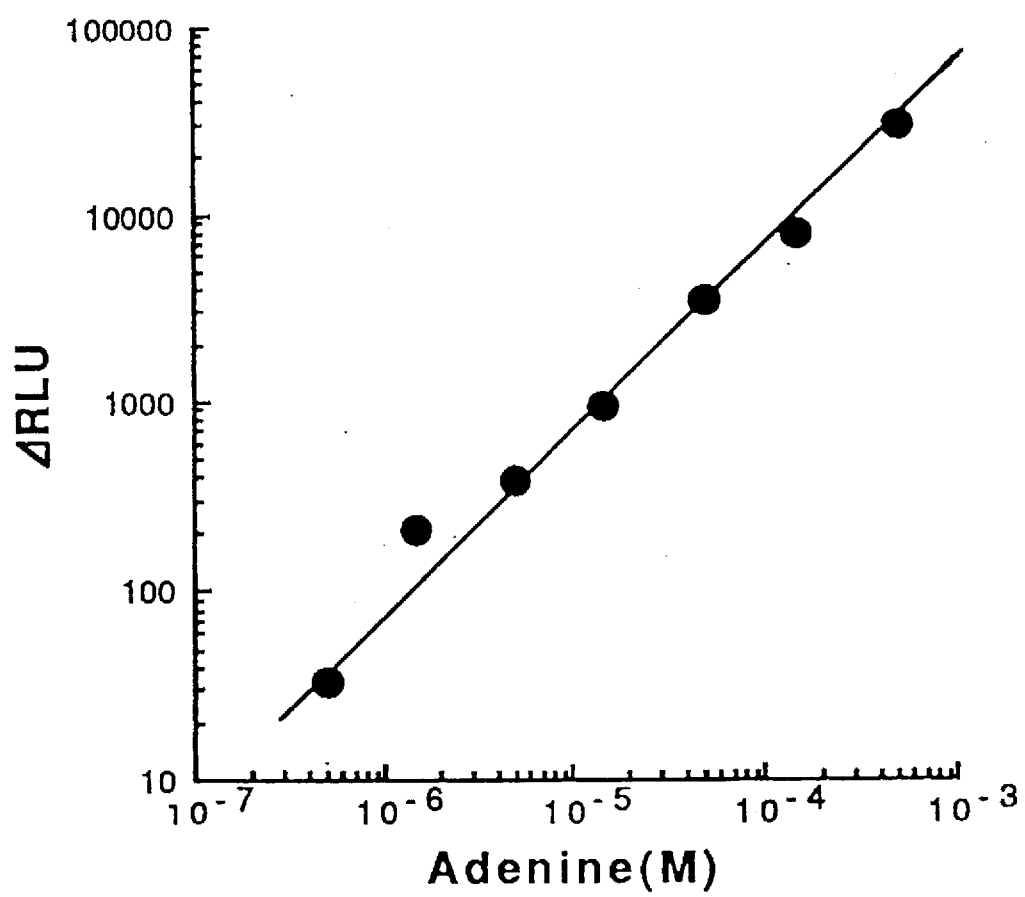
FIG. 2 is a graph showing a calibration curve of adenine when methylglyoxal is used.

When a calibration curve of adenine was prepared from the thus obtained luminescent intensity, a satisfactorily straight line was obtained within the range of from $5 \times 10^{-7}$M to $5 \times 10^{-4}$M as shown in FIG. 2. In the FIG. 2, the axis of abscissa indicates adenine concentration, and the axis of ordinate indicates a value obtained by subtracting the luminescent intensity of blank (no addition of adenine) from the luminescent intensity of each adenine solution having respective concentration.

(Example 3)

Figure 3:
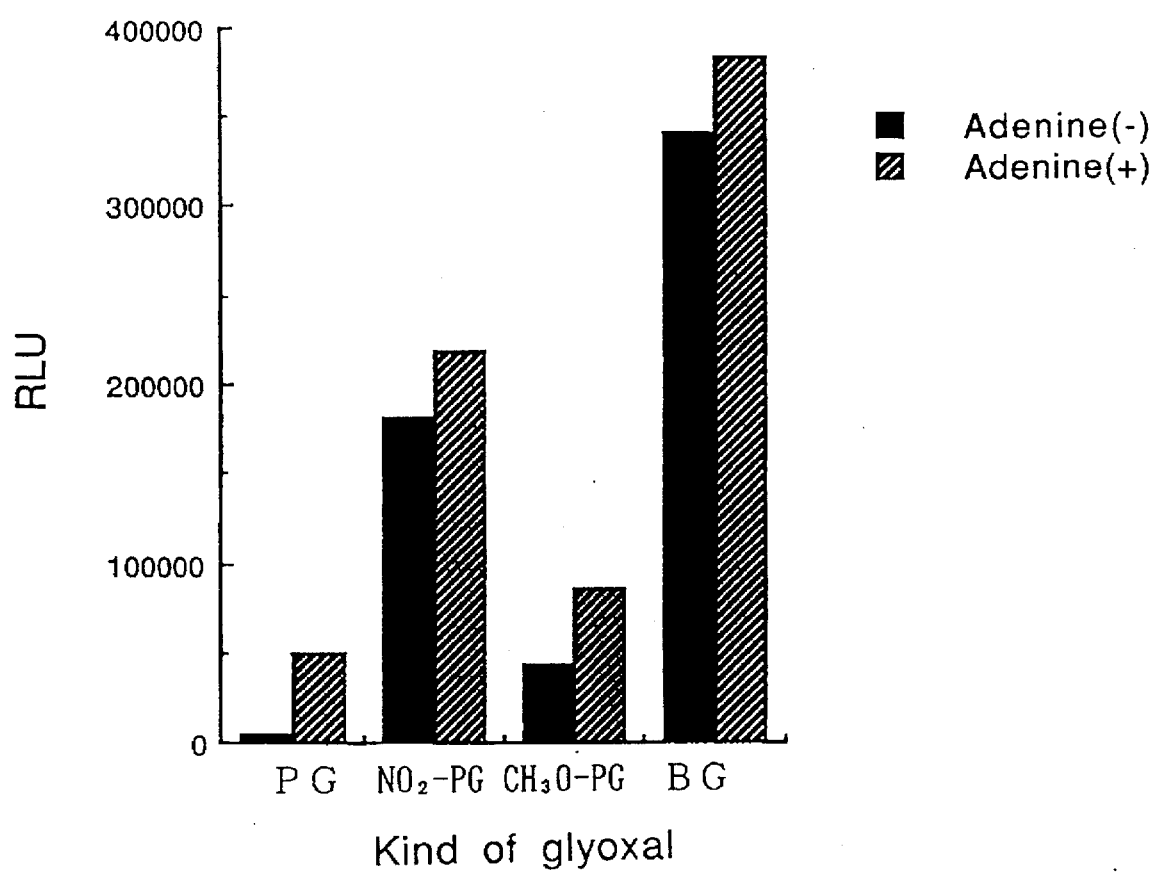
FIG. 3 is a graph showing comparison of increasing rates of luminescent intensity by various glyoxal derivatives.

Luminescent reaction of adenine using various glyoxal compounds and effect of hydrogen peroxide i) Each of 4 kinds of glyoxal derivatives, namely phenylglyoxal (PG) and conventionally synthesized p-nitrophenylglyoxal (NO$_2$—PG), p-methoxyphenylglyoxal (CH$_3$O—PG) and 2-benzofuranylglyoxal (BG), was dissolved in i-PrOH (BG was dissolved in DMSO) to prepare 0.3M solution. Separately from this, adenine was dissolved in a small amount of distilled water and made into a sample of $5 \times 10^{-5}$M with i-PrOH. A 100 μl portion of the sample solution was put in a glass vial, followed by the addition of 50 μl of each of the 0.3M glyoxal compound solution (PG, NO$_2$—PG, CH$_3$O—PG or BG) and 1.2M hydrochloric acid dissolved in i-PrOH, and the vial was then sealed and heated at 100° C. for 1.5 hours. The thus obtained reaction solution was cooled and used for the measurement of chemilumi-nescence in the following manner. A 20 μl of the reaction solution was put in a glass tube for measurement and mixed with 400 μl of DMF containing 50 mM of hydrogen peroxide and 5 mM of 2-ME. After arranging the sample tube in a chemiluminescence analyzer (LB952T/16, Berthold), 300 μl of 0.25M sodium hydroxide aqueous solution was added to the tube to start the luminescent reaction, and the resulting luminescent intensity was measured for 2 seconds just after the addition of the alkaline solution. As shown in FIG. 3, luminescent intensity was found in all of the 4 kinds of glyoxal compounds. In the FIG. 3, adenine (−) indicates luminescent intensity of blank, no addition of adenine, and adenine (+) indicates luminescent intensity of adenine-added sample.

ii) Each of 5 kinds of glyoxal derivatives, namely phenylglyoxal (PG), methylglyoxal (MG) and methylglyoxal dimethylacetal (MGA), and ethylglyoxal dimethylacetal (EGA) and n-butylglyoxal (BuGA) both of which have been synthesized in accordance with the procedure of Serratosa (*Tetrahedron*, vol.16, pp.185–191, 1961), was dissolved in i-PrOH to prepare 0.3M solution. Separately from this, adenine was dissolved in a small amount of distilled water and made into a sample of $5 \times 10^{-4}$M with i-PrOH. A 100 μl of the each sample solution was put in a glass vial, followed by the addition of 50 μl of each of the 0.3M glyoxal compound solution (PG, MG, MGA or BuGA) and 1.2M hydrochloric acid dissolved in i-PrOH, and the vial was then sealed and heated at 100° C. for 1.5 hours. The thus obtained reaction solution was cooled and used for the measurement of chemiluminescence in the following manner. A 10 μl of the reaction solution was put in a glass tube for measurement and mixed with 400 μl of DMF containing 50 mM of hydrogen peroxide and 5 mM of 2-ME. In the same manner, a control sample was prepared by mixing 10 μl of the reaction solution with 400 μl of DMF without addition of hydrogen peroxide. In this instance, a DMF preparation for high performance liquid chromatography (peroxides, max 0.001% (as H$_2$O$_2$)) was used in the above two mixture preparations manufactured by Wako Pure Chemical industries, Ltd.

After arranging the glass tube in a chemiluminescence analyzer (LB952T/16, Berthold), 300 μl of 0.25M sodium hydroxide aqueous solution was added to the tube to start the luminescent reaction, and the relative light units (RLU) was measured for 2 seconds just after the addition of the alkaline solution.

Figure 4:
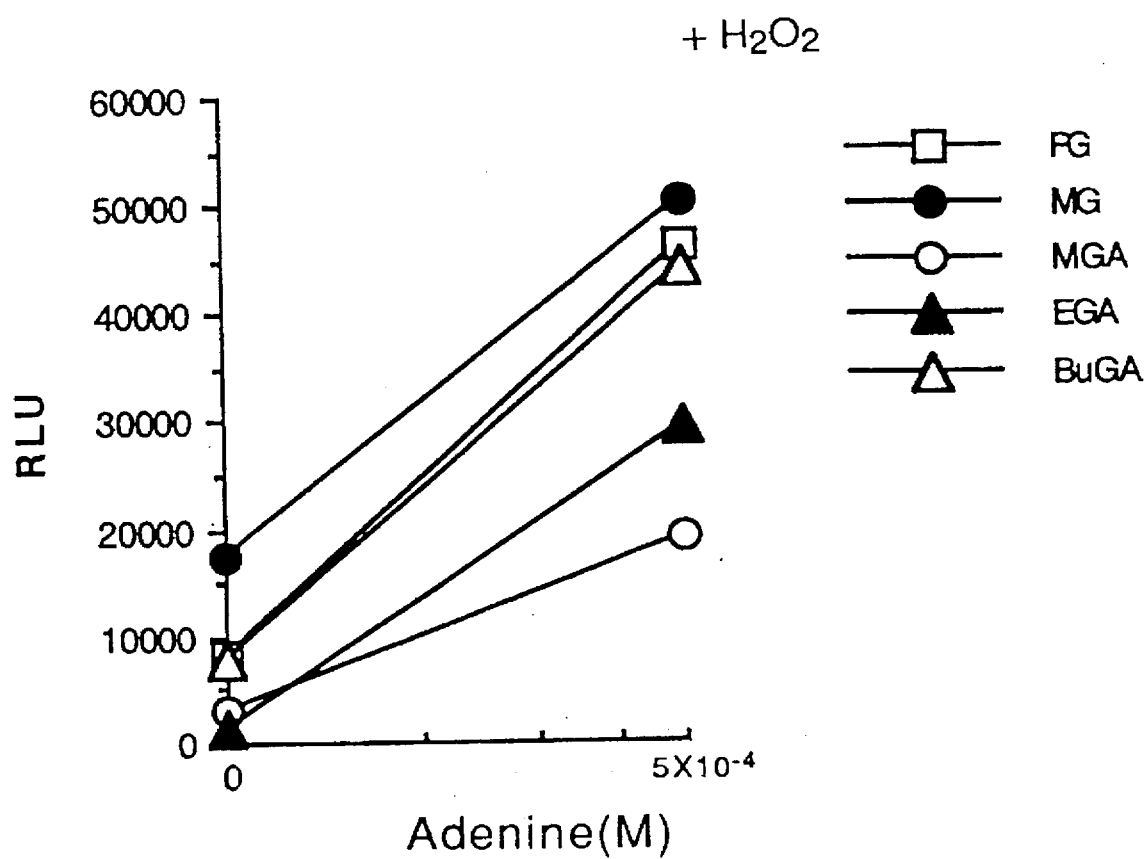
FIG. 4 is a graph showing comparison of increasing rates of luminescent intensity by various glyoxal derivatives in a solvent for luminescence containing hydrogen peroxide.
Figure 5:
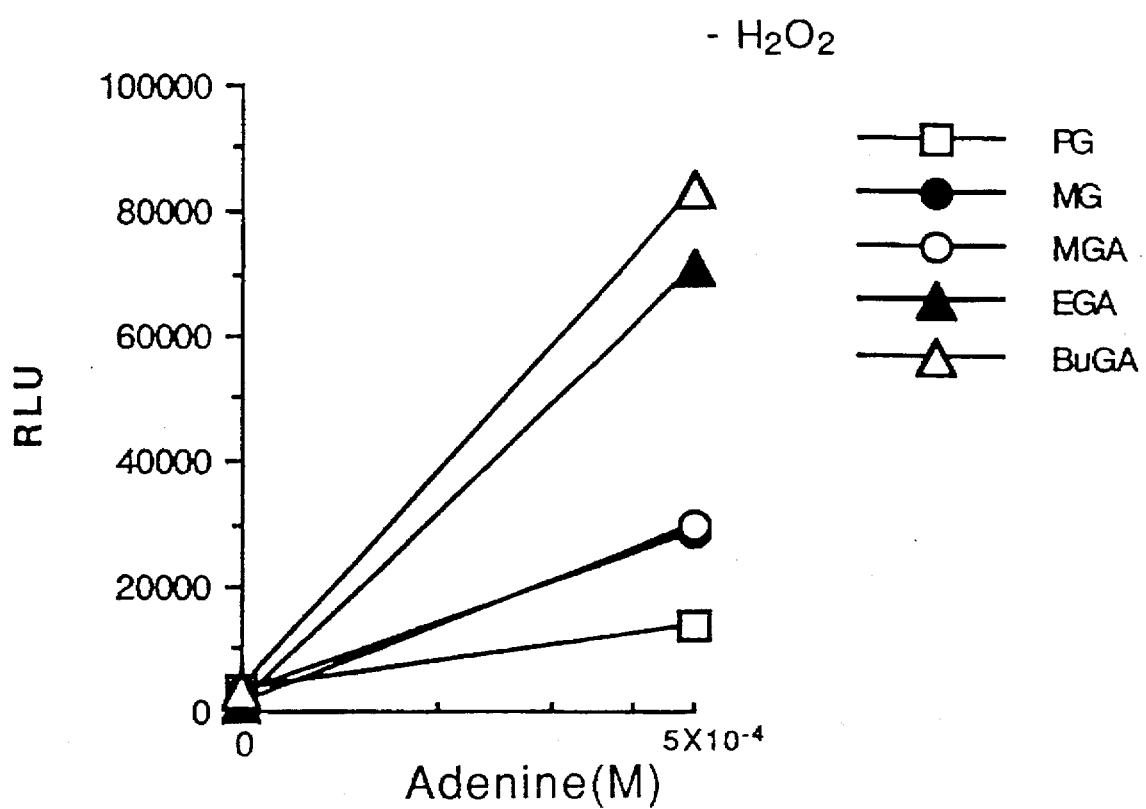
FIG. 5 is a graph showing comparison of increasing rates of luminous intensity by various glyoxal derivatives in a solvent for luminescence which does not contain hydrogen peroxide.

As shown in FIG. 4, luminescent intensity was found in all of the glyoxal compounds MG, MGA, BuGA and PG when DMF containing hydrogen peroxide (50 mM) and 2-ME was used as a solvent for luminescence. On the contrary, when DMF without addition of hydrogen peroxide and was used as a solvent for luminescence, decrease in the luminescent intensity was found in PG, while decrease in the background was found in MG, MGA, EGA and BuGA with increase in the luminescent intensity in MGA, EGA and BuGA (FIG. 5). Using these data, signal noise ratio (S/N ratio) in the case of addition of hydrogen peroxide was compared with that in the case of their absence, and the results were shown in Table 1. While decrease in the S/N ratio was found when hydrogen peroxide was not added in the case of PG which was used as a comparative example, significant increase in the S/N ratio in the case of no addition of hydrogen peroxide was found in each case of MG, MGA, EGA and BuGA. The S/N ratio with no addition of hydrogen peroxide was about 2 times higher in the case of MG, about 6 times higher in MGA, about 5 times higher in EGA and about 4 times higher in BuGA, than the case of the comparative example in which PG was used as the compound and hydrogen peroxide was added to the solvent for luminescence. Data shown in Table 1 indicate S/N ratios.

TABLE 1

Comparison of S/N ratio

Solvent for luminescence (DMF)

| Compound | Addition of 2-ME and $H_2O_2$ | No addition |
|---|---|---|
| PG | 5.6 | 3.9 |
| MG | 2.9 | 10.4 |
| MGA | 6.5 | 33.8 |
| EGA | 10.6 | 50.3 |
| BuGA | 5.7 | 22.9 |

Note)
DMF: N,N-dimethylformamide (HPLC grade, peroxides, max 0.001% (as $H_2O_2$)) manufactured by Wako Pure Chemical Industries, Ltd.

(Example 4)

Measurement of various nucleic acid bases using phenylglyoxal i) As adenyl group-containing substances, measurement of adenine, adenosine, DNA (salmon sperm DNA, Pharmacia) and RNA (Type XI, baker's yeast origin, Sigma) was carried out. Each of these samples was dissolved in a small amount of distilled water and diluted with i-PrOH to prepare a sample solution. A 100 µl of each sample solution was put in a glass vial, followed by the addition of 50 µl of each of 0.3M PG and 1.2M hydrochloric acid dissolved in i-PrOH, and the vial was then sealed and heated at 100° C. for 1.5 hours. The thus obtained reaction solution was cooled and used for the measurement of chemiluminescence in the following manner. A 20 µl of the reaction solution was put in a glass tube for measurement and mixed with 400 µl of DMF containing 50 mM of hydrogen peroxide and 5 mM of 2-ME. After arranging the glass tube in a chemiluminescence analyzer (LB952T/16, Berthold), 300 µl of 0.25M sodium hydroxide aqueous solution was added to the tube to start the luminescent reaction, and the resulting luminescent intensity was measured for 2 seconds just after the addition of the alkaline solution. As shown in Table 2, generation of luminescence was found in all of the tested adenyl group-containing substances.

TABLE 2

| Substance | Sample conc. | ΔRLU |
|---|---|---|
| Adenine | $5 \times 10^{-7}$ M | 33330 |
| Adenosine | $5 \times 10^{-7}$ M | 33031 |
| DNA | 50 µg/ml | 26564 |
| RNA | 50 µg/ml | 57628 | ii) Guanine, thymine, cytosine, uracyl, guanosine, cytidine, thymidine and uridine were used as substances which do not contain adenyl group, and each of the substances was dissolved in a small amount of distilled water and diluted with i-PrOH to prepare a sample solution containing $5 \times 10^{-5}$M of each substance. When 100 µl of each sample solution was subjected to the luminescent reaction in accordance with the standard protocol described in Example 1 and the resulting chemiluminescence intensity was measured, no generation of luminescence was observed in these substances which do not contain adenyl group. The results are shown in Table 3 in which the ΔRLU ratio means ΔRLU of each test sample per ΔRLU of adenine which defined as 100.

TABLE 3

| Substance | Conc. | ΔRLU ratio | Compound | Conc. | ΔRLU ratio |
|---|---|---|---|---|---|
| Adenine | $5 \times 10^5$ M | 100 | Adenosine | $5 \times 10^{-5}$ M | 105 |
| Guanine | $5 \times 10^5$ M | 0 | Guanosine | $5 \times 10^{-5}$ M | 0 |
| Cytosine | $5 \times 10^5$ M | 0 | Cytidine | $5 \times 10^{-5}$ M | 0 |
| Thymine | $5 \times 10^5$ M | 0 | Thymidine | $5 \times 10^{-5}$ M | 0 |
| Uracyl | $5 \times 10^5$ M | 0 | Uridine | $5 \times 10^{-5}$ M | 0 |

(Example 5)

Measurement of various nucleic acid bases and nucleic acids using methylglyoxal dimethylacetal In order to examine substrate specificity of luminescent reaction of adenine when methylglyoxal dimethylacetal is used, adenine, adenosine and Poly (A) (product No. 108626, Boehringer-Mannheim) as adenyl group-containing substances and guanosine, Poly (U) (product No. 108928, Boehringer-Mannheim) and Poly (dT) (product No. 27-7834, Pharmacia) as adenyl group-free substances was dissolved in a small amount of distilled water and diluted with i-PrOH to prepare sample solutions of adenine, adenosine and guanosine, each having a concentration of $1 \times 10^{-4}$ M, and of Poly (A), Poly (U) and Poly (dT), each having a concentration of 100 µg/ml.

Figure 6:
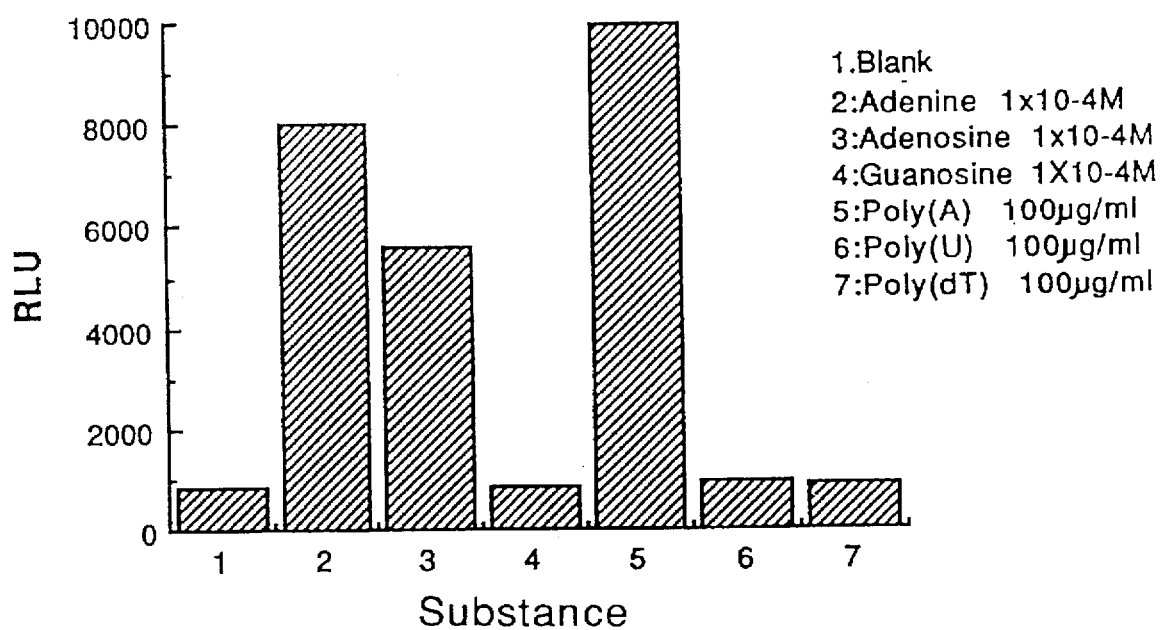
FIG. 6 is a graph showing reactivities of methylglyoxal with various nucleic acid bases and nucleic acids.

As shown in FIG. 6, when 100 µl of each sample solution was subjected to the luminescent reaction in accordance with the protocol described in Example 2 and the resulting chemiluminous intensity was measured, no release of luminescence was observed in the substances which do not contain adenyl group.

(Example 6)

Effect of 2-ME in solvent for luminescence

A sample containing 0 or 100 µg/ml of Poly (A) was subjected to the reaction described in Example 2, and the resulting reaction solution was used for the examination of the effect of 2-ME in solvent for chemiluminescence. A 10 µl portion of each reaction solution was put in a glass tube for measurement and mixed with 400 µl of DMF containing varied amount of 2-ME (0 to 500 mM).

Figure 7:
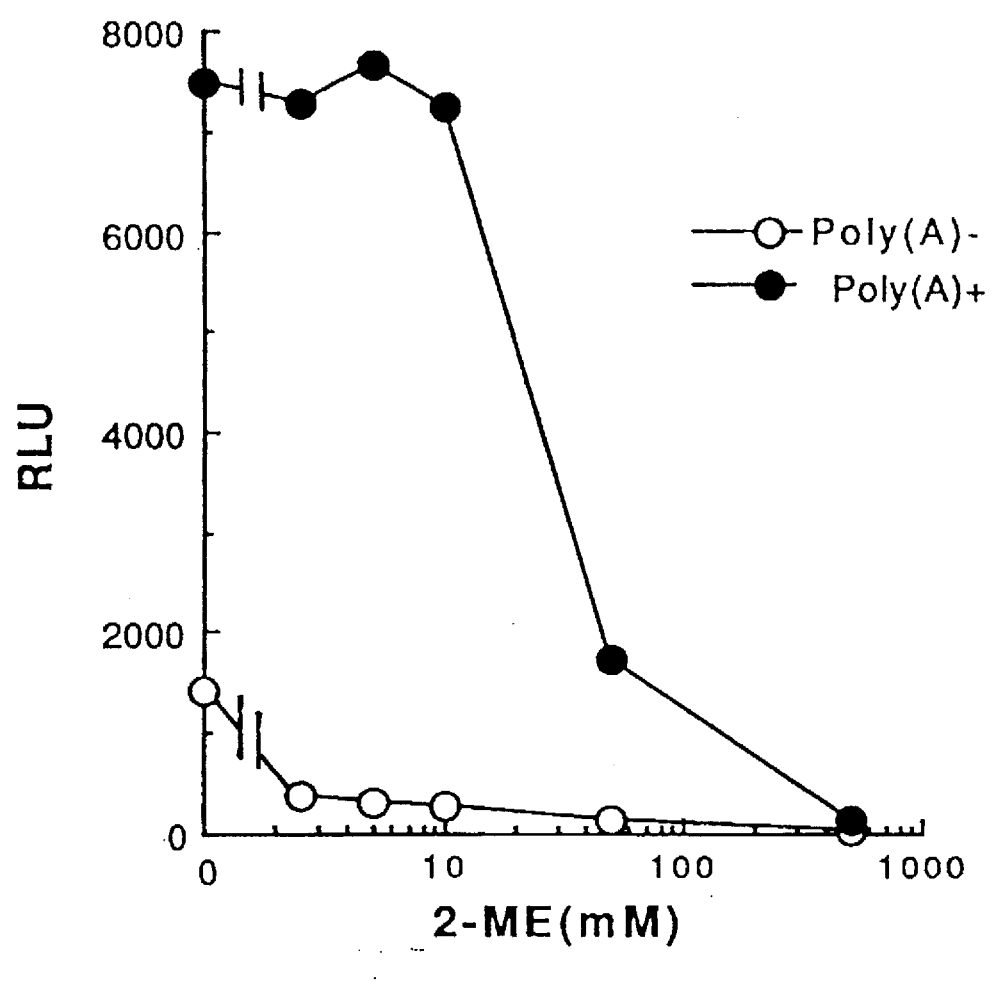
FIG. 7 is a graph showing effects of 2-ME in a solvent for luminescence.

When the glass tube was arranged in a chemiluminescence analyzer and the intensity of luminescence was measured in accordance with the procedure described in Example 2, it was found that the blank value decreased at a 2-ME concentration of 2.5 to 10 mM and the S/N ratio was improved about 5 times in comparison with the case of no addition of 2-ME (FIG. 7).

Analysis of the results shown in FIG. 7 in combination with the results shown in FIGS. 4 and 5 indicates that the decreased blank value and improved S/N ratio observed in MG, MGA and BuGA of FIG. 5 are due to the addition of no oxidizing agent.

(Example 7)

Figure 8:
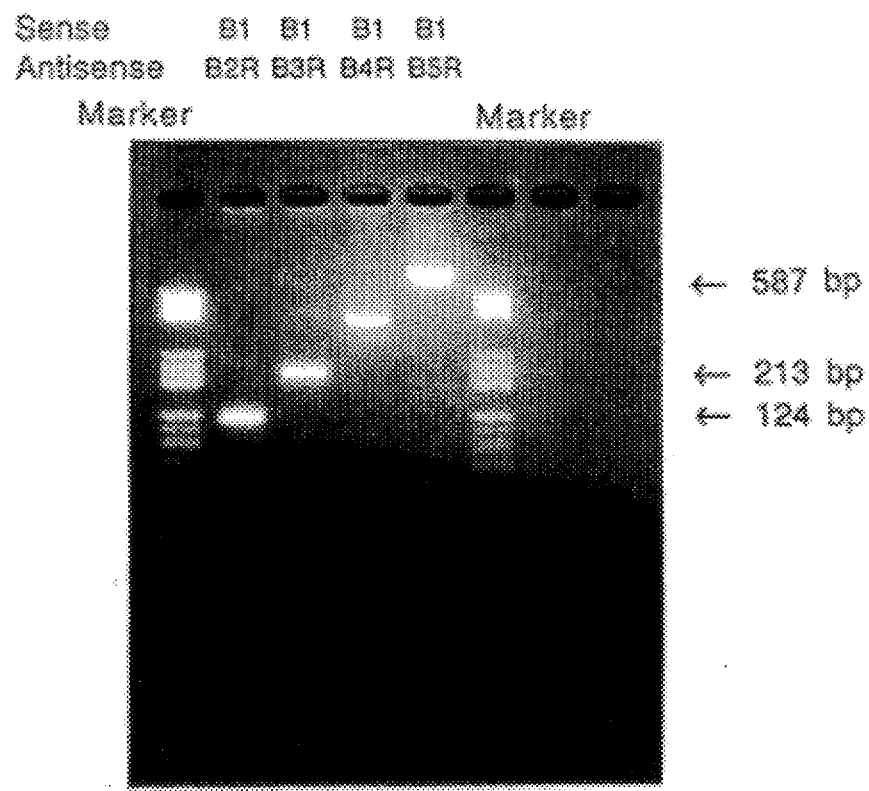
FIG. 8 is a picture showing results of electrophoresis.

Application to the measurement of PCR amplification product 7-1 Length of amplified product and luminescent intensity As shown in Table 4, five sequences specific for hepatitis B virus were selected from the C region gene sequence (GenBank accession number, X01587) of a hepatitis B virus genomic DNA (HBV-DNA). In order to attain efficient incorporation of adenine into PCR amplification products, primers designed by 10 mer of thymine linking to 5' side of each of the selected sequences were prepared using a DNA synthesizer (DNA/RNA Synthesizer 394, Applied Biosystems). Dane particles were purified from plasma of an HBe antigen-positive chronic hepatitis B patient (serotype, adr) in accordance with the procedure of A. Fujiyama et al. (*Nucleic Acids Research*, vol.11 (13), p.4601–1983) to isolate HBV-DNA (3.2 kb). The thus obtained DNA fragment was cloned into a plasmid (pBR 322), and the resulting recombinant (pBR-HBV) was purified to be used as a test sample. Using 100 ng of the pBR-HBV as a test sampler amplification was carried out by adding 2.5 units of Amplitaq™ DNA polymerase (Perkin-Elmer Cetus) to 100 µl of a Taq reaction solution (10 mM Tris-HCl (pH 8.3), 1.5 mM MgCl$_2$, 50 mM KCl, 200 µM of each dNTP and 0.2 µg of each primer), adding one drop of mineral oil to the resulting mixture and then repeating 35 reaction cycles, each cycle consisting of a series of reactions at 94° C. for 1 minute, at 55° C. for 1 minute and at 72° C. for 1 minute in that order, using DNA Thermal Cycler (Perkin-Elmer Cetus). A 5 µl of each reaction product was subjected to electrophoresis using 4% Nusieve™-GTG agarose gel (FMC Bioproducts) containing 0.5 µg/ml of ethidium bromide to confirm bands of amplified products. As the results, amplified products having intended lengths were obtained from 4 respective primer combinations (FIG. 8). In this instance, FIG. 8 shows results of electrophoresis carried out for the detection of PCR amplification products with respective combinations of primers.

Figure 9:
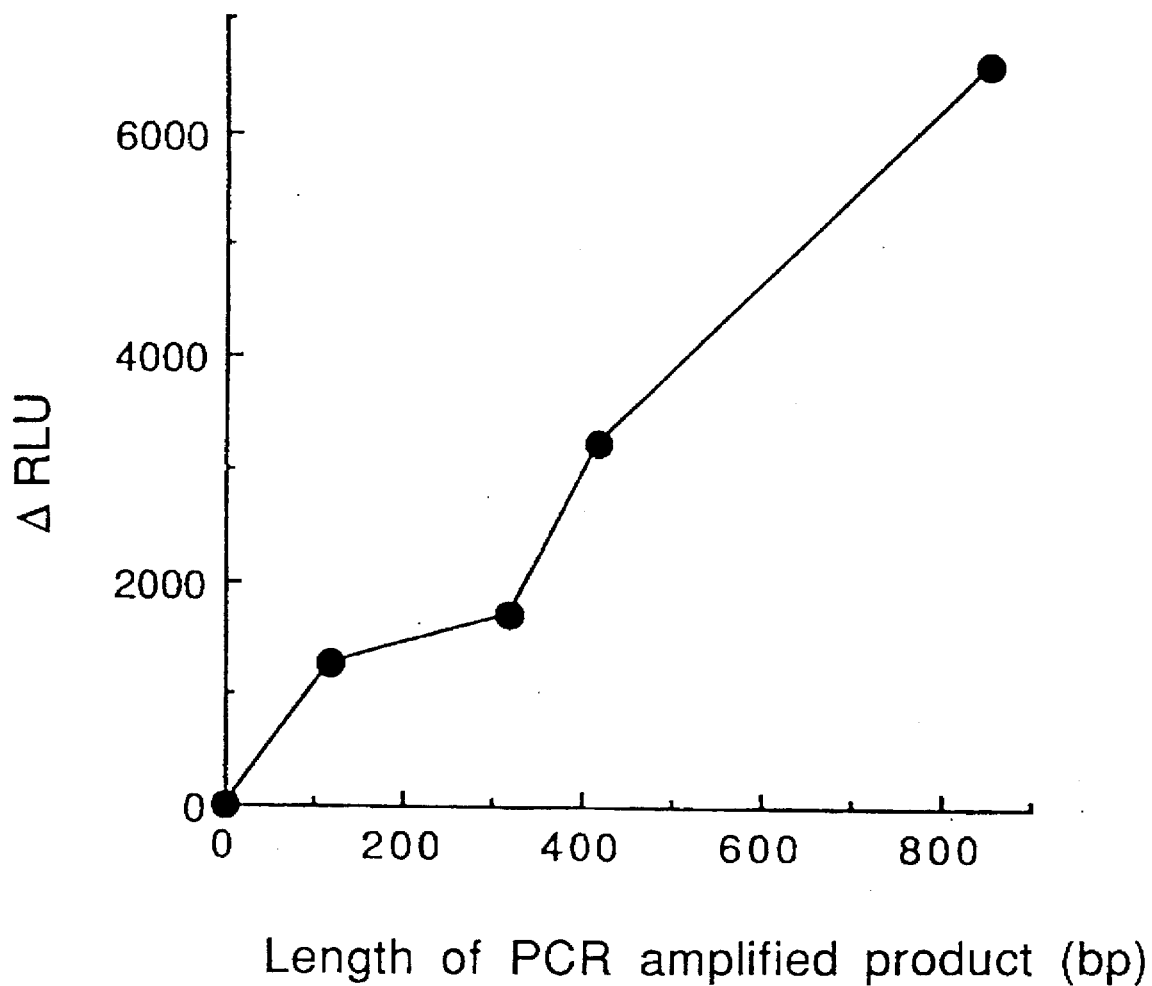
FIG. 9 is a graph showing a relationship between the chain length of a PCR product and the chemiluminescent intensity.

Next, 25 µl of 5M NaCl and 84 µl of i-PrOH were added to 80 µl of the reaction product, and the mixture was allowed to stand still for 10 minutes on an ice bath to precipitate the amplified product. The thus precipitated amplified product was collected by centrifugation (15,000 rpm for 10 minutes) and dissolved in 5 µl of distilled water to which 95 µl of i-PrOH was subsequently added. A 100 µl of the thus prepared sample solution was put in a glass vial, followed by the addition of 0.3M PG and 1.2M hydrochloric acid dissolved in i-PrOH, and the vial was then sealed and heated at 100° C. for 1.5 hours. The thus obtained reaction solution was cooled and used for the measurement of chemiluminescence in the following manner. A 20 µl portion of the reaction solution was put in a glass tube for measuring use and mixed with 400 µl of DMF containing 50 mM of hydrogen peroxide and 5 mM of 2-ME. After arranging the glass tube in a chemiluminescence analyzer (LB952T/16, Berthold), 300 µl of 0.25M sodium hydroxide aqueous solution was added to the tube to start the luminescent reaction, and the resulting luminescent intensity was measured for 2 seconds just after the addition of the alkaline solution. As shown in FIG. 9, the luminescent intensity increased in proportion to the length of the amplified product.

TABLE 4

| Primer | Sequence (5'-3') | Position | Amplified PCR product chain length | Sequence ID No. |
|---|---|---|---|---|
| Sense |  |  |  |  |
| B1 | (T)$_{10}$-CTCTGCCTAATCATCTCATG | 1701–1720 | — | 1 |
| Antisense |  |  |  |  |
| B2R | (T)$_{10}$-CAAATTCTTTATACGGGTCA | 1781–1800 | 120 bp | 2 |
| B3R | (T)$_{10}$-TCTAAGGCCTCCCGATATAG | 1881–2000 | 320 bp | 3 |
| B4R | (T)$_{10}$-AAGTAAGACAGGAAATGTGA | 1981–2100 | 420 bp | 4 |
| B5R | (T)$_{10}$-TAGGATAGAACCTAGCAGGC | 2511–2530 | 850 bp | 5 |

7-2 Detection of PCR amplification product

Figure 10:
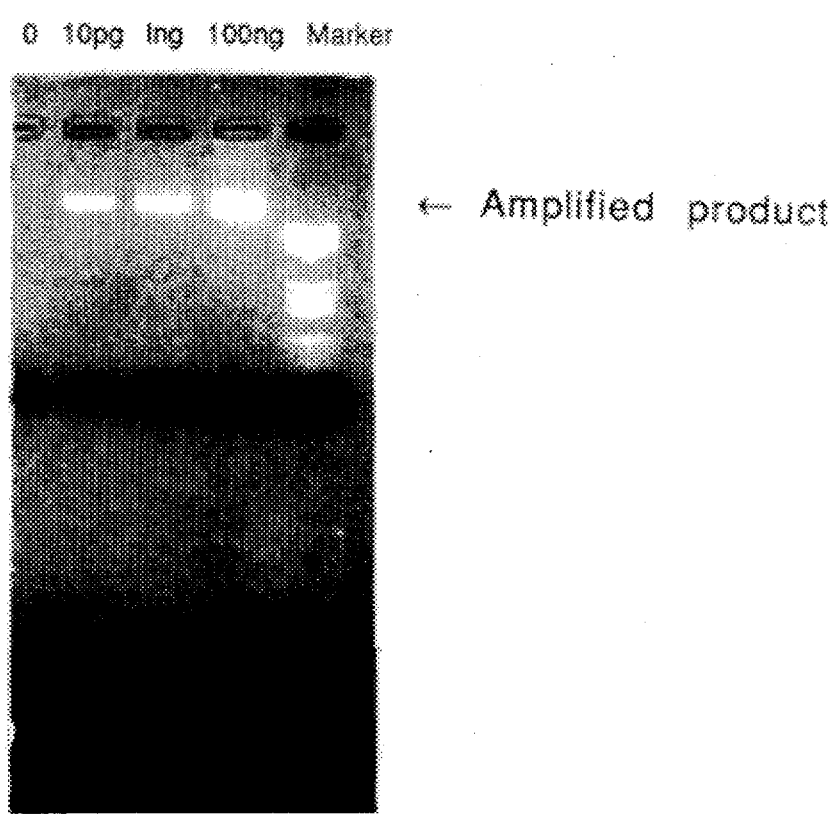
FIG. 10 is a picture showing results of electrophoresis.
Figure 11:
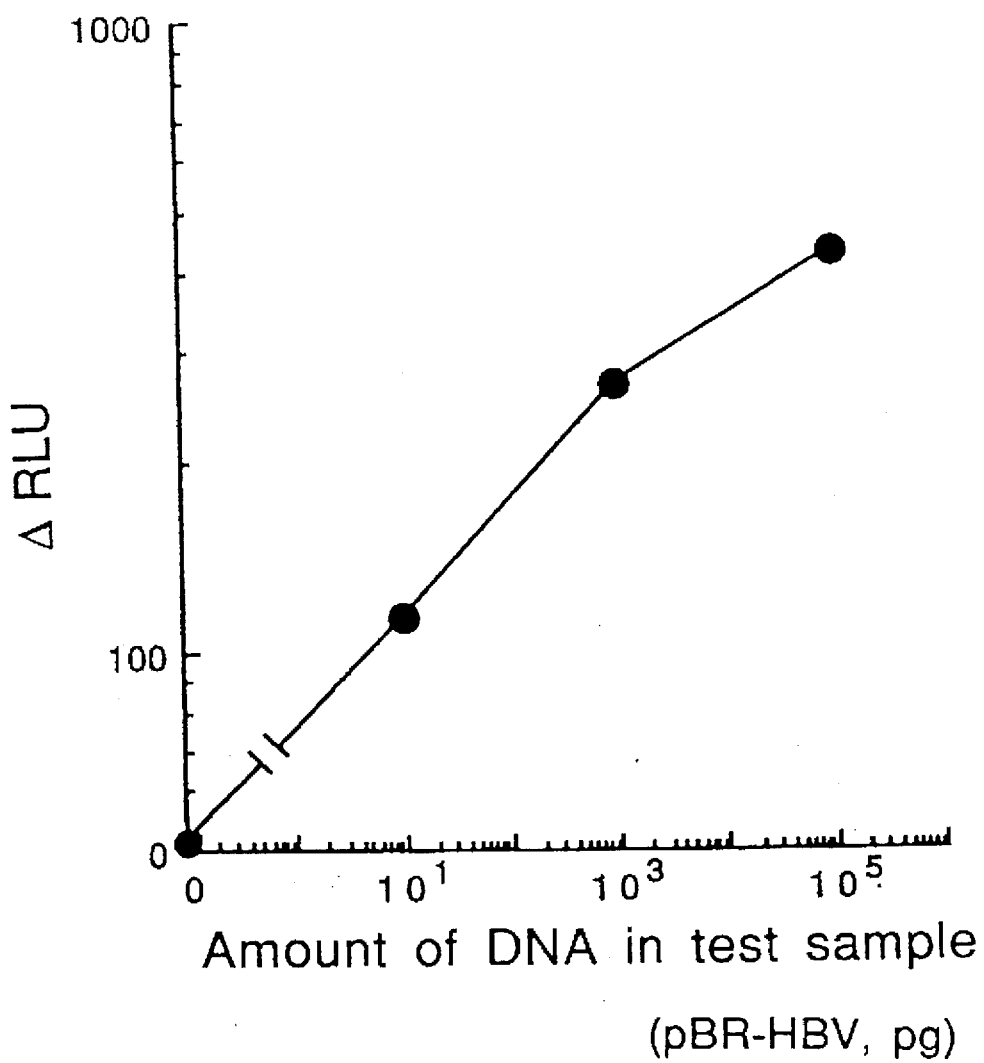
FIG. 11 is a graph showing a relationship between the amount of DNA in a sample and the luminescent intensity of a PCR amplification product.

Using B1and B4R (amplification length, 850 bp) as primers and pBR-HBV (0, 10 pg, 1 ng and 100 ng) as test samples, PCR was carried out under the same conditions as described in Example 7-1, and 5 µl portion of each reaction product was subjected to electrophoresis using 4% Nusieve™-GTG agarose gel (FMC Bioproducts) containing 0.5 µg/ml of ethidium bromide to confirm band of amplified products (FIG. 10). In this instance, FIG. 10 shows results of electrophoresis carried out for the detection of PCR amplification products. The amplified product became dense in proportion to the concentration of pBR-HBV in the sample. Next, 25 µl of 5M NaCl and 84 µl of i-PrOH were added to 80 µl of the reaction product, and the mixture was allowed to stand still for 10 minutes on an ice bath to precipitate of the amplified product. The thus precipitated amplified product was collected by centrifugation (15,000 rpm for 10 minutes) and dissolved in 5 µl of distilled water to which 95 µl of i-PrOH was subsequently added. The thus obtained sample solution was allowed to react with PG in accordance with the protocol described in Example 7-1 to measure intensity of chemiluminescence. As the results, the DNA in the sample was able to be measured even at the amount of 10 pg, and the luminescent intensity after amplification increased as the amount of DNA increased (FIG. 11).

(Example 8)

Calibration curve of nucleic acid

Examination was made on the application of the specific adenine measuring method to a quantitative detection method of nucleic acids.

As shown in Table 5, E0001 (sequence number, 1518-1537) as a sense primer and E1000R (sequence number 2498-2517) as an antisense primer were selected from the ribosomal RNA gene sequence (EMBL accession number, V00348) of *Escherichia coli*(*E. coli*) genomic DNA, and synthesized using a DNA synthesizer (DNA/RNA Synthesizer 394, Applied Biosystems). A genomic DNA sample was prepared from an *E. coli* strain (JM109, Takara Shuzo Co., Ltd.) in accordance with the procedure of Y. Kuchino et al. (*Preparation of Bacterial DNA, Gene.Protein Handling and Blotting*, p.32, 1987, Soft Science), and DNA concentration in the sample was measured based on its absorption at 260 nm. Using 100 ng of the sample, amplification was carried out by adding 2.5 units of Amplitaq™ DNA polymerase (Perkin-Elmer Cetus) to 100 µl of a Taq reaction solution (10 mM Tris-HCl (pH 8.3), 1.5 mM MgCl$_2$, 50 mM KCl, 200 µM of each dNTP and 0.2 µg of each primer), adding one drop of mineral oil to the resulting mixture and then repeating 30 reaction cycles, each cycle consisting of a series of reactions at 94° C. for 1 minute, at 55° C. for 1 minute and at 72° C. for 2 minute in that order, using DNA Thermal Cycler (Perkin-Elmer Cetus), thereby effecting amplification of a 1 kb DNA fragment (sequence number 1518-2517) inserted between E0001 and E1000R.

TABLE 5

| Primer nucleotide sequence | | |
|---|---|---|
| Primer | Sequence (5'-3') | Sequence ID No. |
| E0001 | AAATTGAAGAGTTTGATCAT | 6 |
| E1000R | TGGATGTCAAGACCAGGTAA | 7 |

Next, a 100 µl of the thus obtained reaction solution was mixed thoroughly with 100 µl of a 1:1 mixture solution of phenol (saturated with 1M Tris, pH 8.0) and chloroform, and the mixture was centrifuged at 15,000 rpm for 15 seconds to collect the resulting water phase. The thus collected water phase was again extracted with the phenol-chloroform (1:1) solution, and the extract was mixed thoroughly with 100 µl of chloroform to collect the resulting water phase. To this were added 10 µl of 3M sodium acetate (pH 5.2) and 220 µl of ethanol (−20° C.), and the resulting mixture was allowed to stand still overnight at −20° C. to precipitate of the amplified product. After centrifugation at 15,000 rpm for 10 minutes, the supernatant was discarded and the resulting precipitate was vacuum-dried. Thereafter, the thus obtained amplified product was dissolved in 10 µl of distilled water, and DNA concentration in the solution was calculated based on the absorbance at 260 nm. The thus prepared solution was diluted with i-PrOH to be used as a sample solution.

Figure 12:
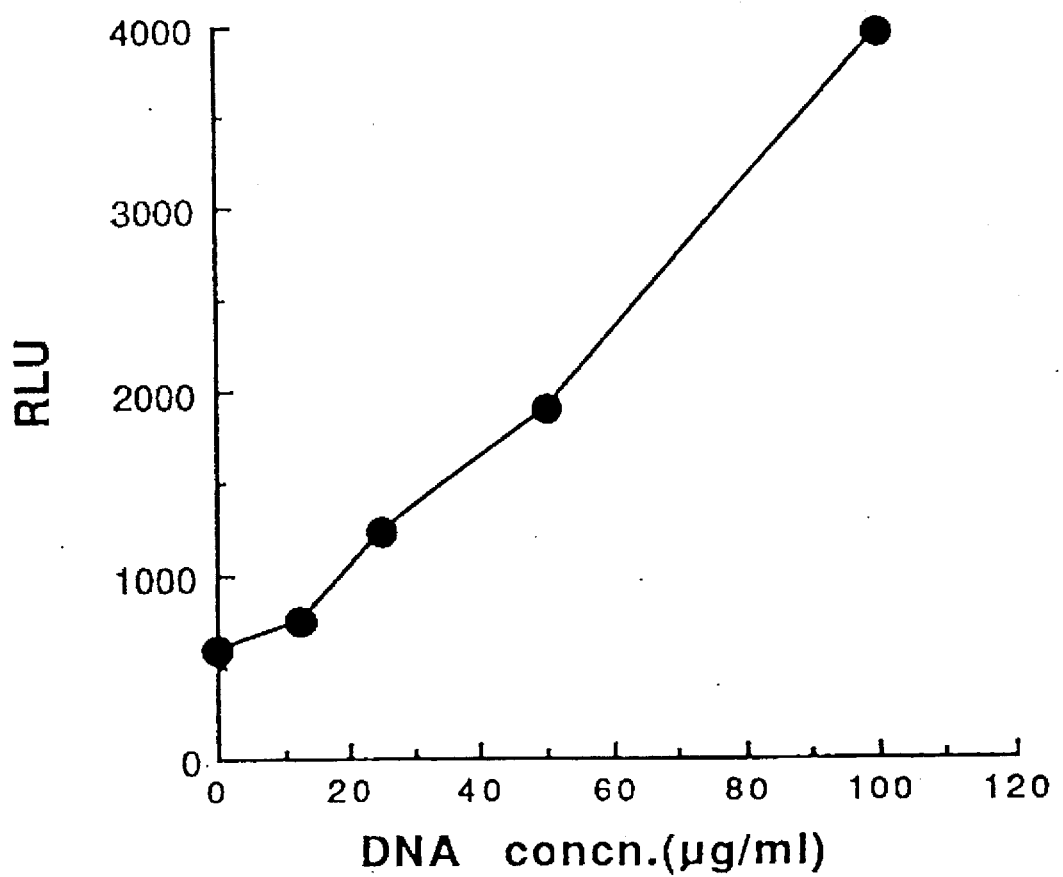
FIG. 12 is a graph showing a relationship between the DNA concentration of an amplification product prepared by PCR and the intensity of chemiluminescence.

When the sample solution was subjected to its reaction with MGA in accordance with the protocol of Example 2, the measured intensity of chemiluminescence showed a proportional relation to the concentration of DNA (FIG. 12).

(Example 9)

Calibration curve of DNA using various glyoxal compounds in the same manner as described in Example 7-1 using 100 ng of pBR-HBV obtained in Example 7-1 as a test sampler PCR was carried out using primers B1 and B4R (amplification length, 850 bp).

Next a 100 µl of the thus obtained reaction solution was mixed thoroughly with 100 µl of a 1:1 mixture solution of phenol (saturated with 1M Tris, pH 8.0) and chloroform, and the mixture was centrifuged at 15,000 rpm for 15 minutes to collect the resulting water phase. The thus collected water phase was again extracted with the phenol-chloroform (1:1) solution, and the extract was mixed thoroughly with 100 µl of chloroform to collect the resulting water phase. To this water phase were added 10 µl of 3M sodium acetate (pH 5.2) and 220 µl of ethanol (−20° C.), and the resulting mixture was allowed to stand still overnight at −20° C. to precipitate of the amplified product. After centrifugation at 15,000 rpm for 10 minutes, the supernatant was discarded and the resulting precipitate was vacuum-dried. Thereafter, the thus obtained amplified product was dissolved in 10 µl of distilled water, and DNA concentration in the solution was calculated based on the absorbance at 260 nm. The thus prepared solution was diluted with distilled water to prepare a sample solution of 0, 10, 50, 100, 250 or 500 ng/2 µl sample.

Figure 13:
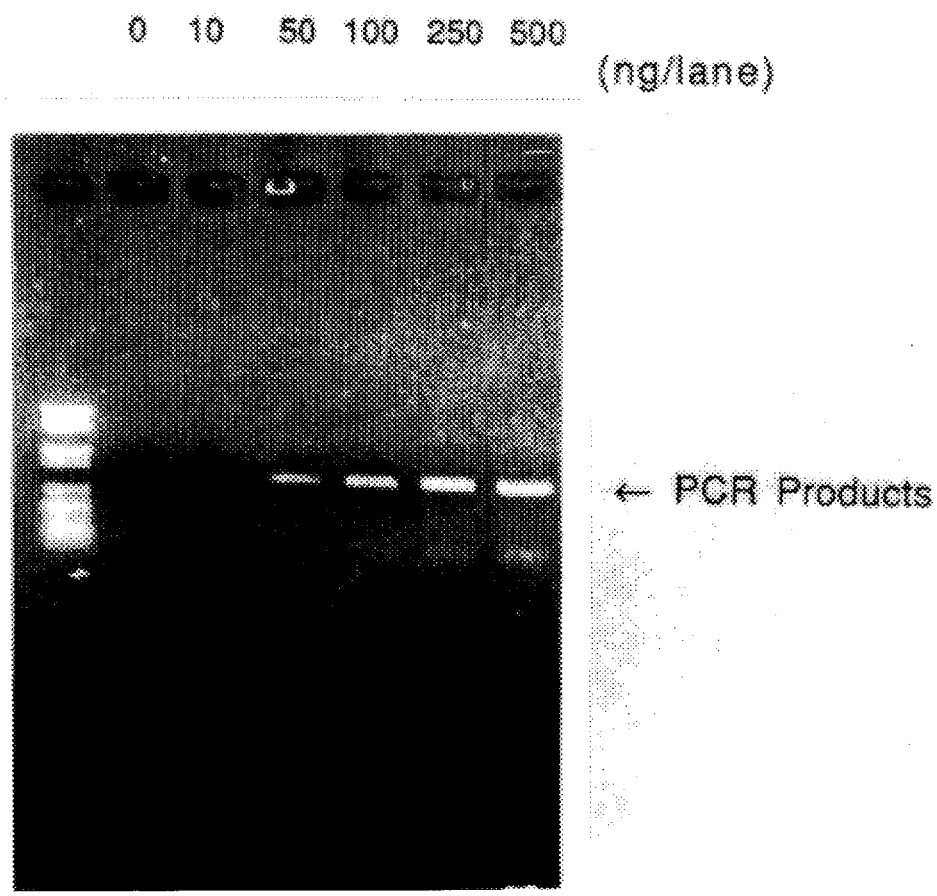
FIG. 13 is a picture showing results of electrophoresis.

Next, 2 µl of each sample solution was subjected to electrophoresis using 1% agarose gel containing 0.5 µg/ml of ethidium bromide for detecting the sensitivity of the ethidium bromide method (FIG. 13).

Figure 14A:
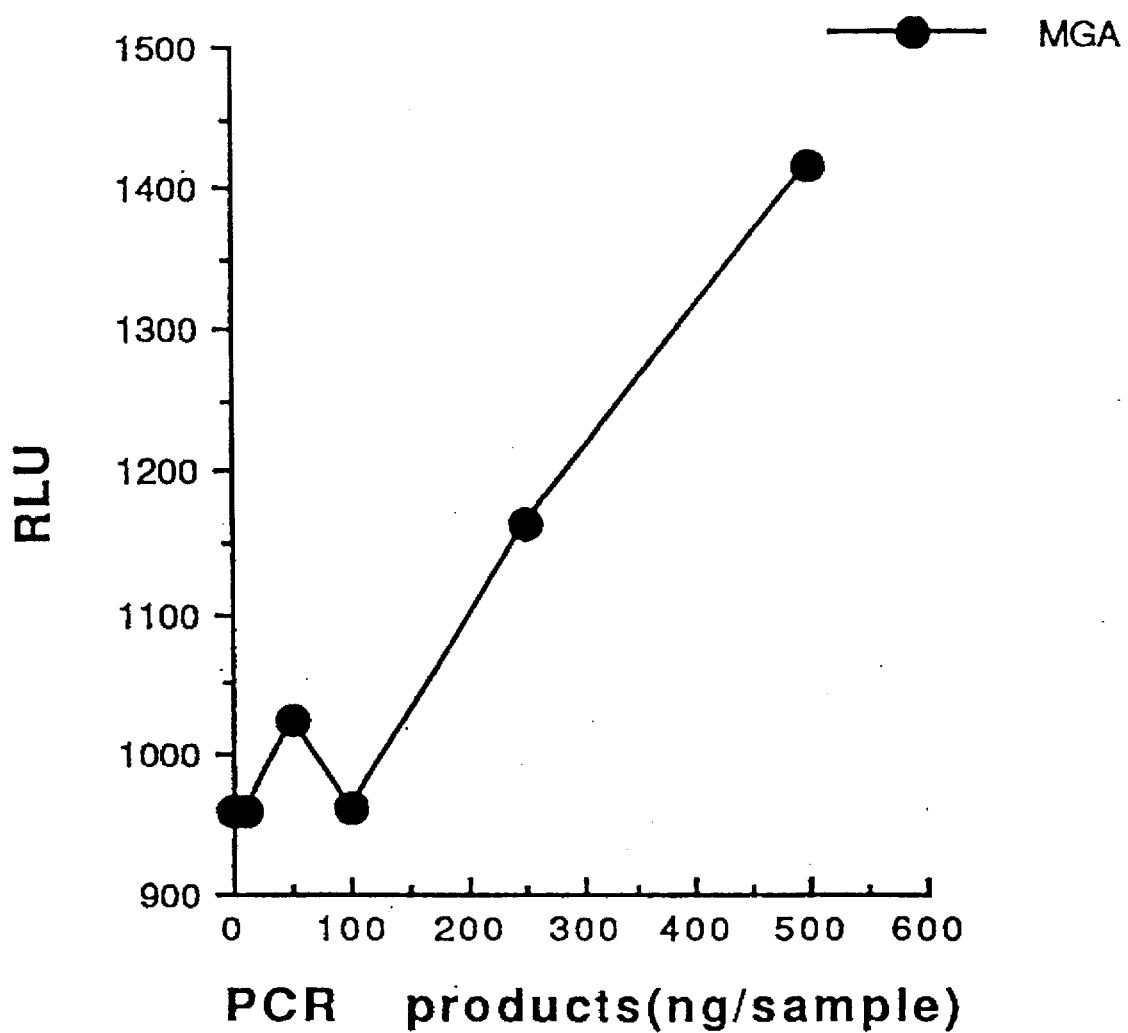
FIG. 14 a, b and c are graphs showing a relationship between the amount of amplified products prepared by PCR and the intensity of chemiluminescence when respective glyoxal compounds are used.
Figure 14B:
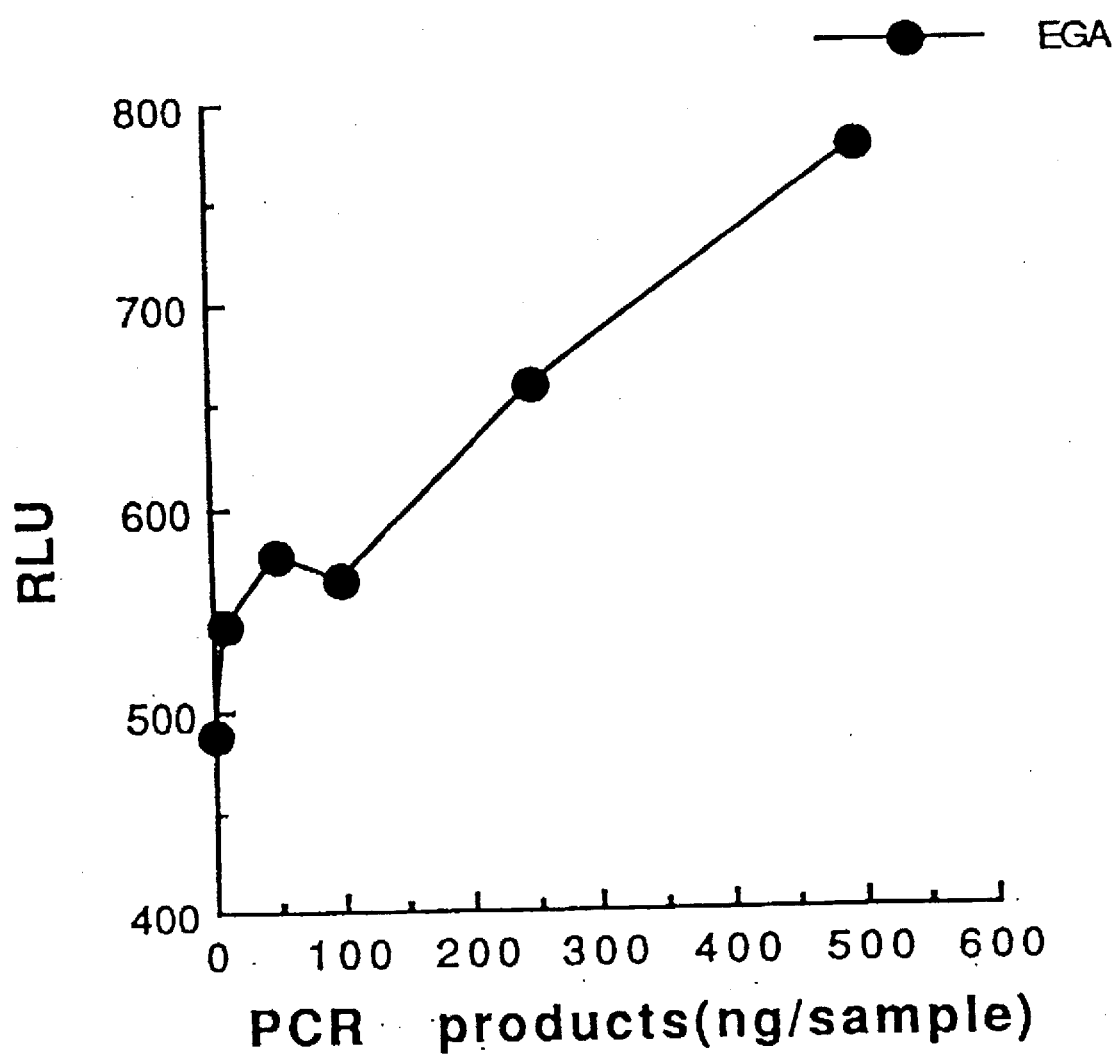
Figure 14C:
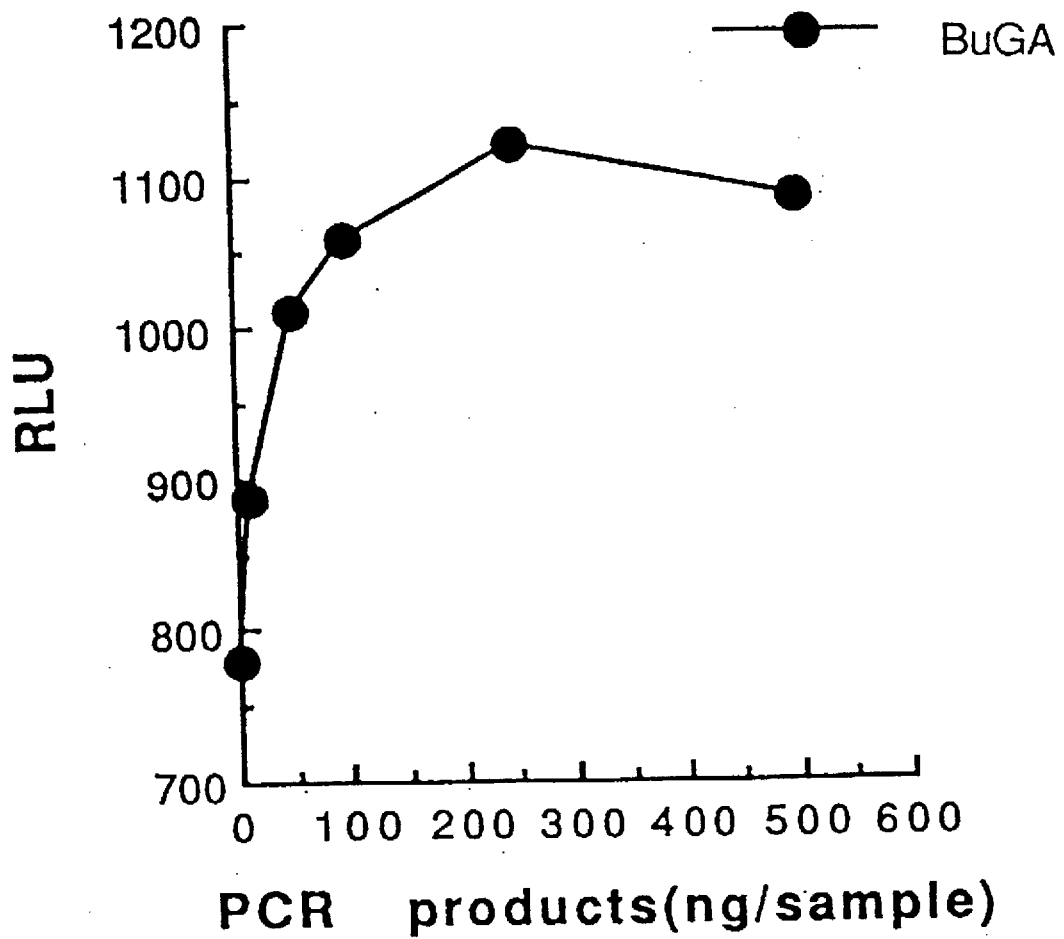

A 2 µl of each sample solution was put in a glass vial, followed by adding each of 50 µl of 0.05M glyoxal compounds (EGA, BuGA) or 0.3M glyoxal compound (MGA), and 1.2M hydrochloric acid dissolved in i-PrOH, and the vial was then sealed and heated at 100° C. for 1.5 hours. The thus obtained reaction solution was cooled and used for the measurement of chemiluminescence in the following manner. A 10 µl portion of the reaction solution was put in a glass tube for measurement and mixed with 400 µl of DMF containing 2 mM of L-cysteine. After arranging the glass tube in a chemiluminescence analyzer (LB952T/16, Berthold), 300 µl of 0.25M sodium hydroxide aqueous solution was added to the tube to start the luminescent reaction, and the resulting luminescent intensity was measured for 2 seconds just after the addition of the alkaline solution. The resulting chemiluminous intensity was measured, the luminescent intensity showed a proportional relation to the amount of DNA, and the detection sensitivity was found to be about 250 ng/sample in the case of MGA, and about 10 ng/sample in EGA and BuGA (FIG. 14 a, b and c). In contrast, the detection sensitivity of ethidium bromide method resulted in 50 ng/sample.

Example 10

Application to a measuring method of PCR amplification product i) A method using dUTP-biotin Using B1 and B5R (amplification length, 850 bp) as primers and 0 ng (negative control) or 100 ng (positive control) of the pBR-HBV obtained in Example 7-1 as a test sample, PCR was carried out by adding 2.5 units of Amplitaq™ DNA polymerase (Perkin-Elmer Cetus) to 100 µl of a Taq reaction solution (10 mM Tris-HCl (pH 8.3), 1.5 mM MgCl$_2$, 50 mM KCl, 100 µM of dATP, dGTP and dCTP, 75 µM of dTTP, 25 µM of biotin-16-dUTP (Boehringer-Mannheim) and 0.2 µg of each primer), adding one drop of mineral oil to the resulting mixture and then repeating 30 reaction cycles, each cycle consisting of a series of reactions at 94° C. for 1 minute, at 55° C. for 1 minute and at 72° C. for 1 minute in that order, using DNA Thermal Cycler (Perkin-Elmer Cetus).

Each of the reaction solutions (6.25, 12.5, 25 or 50 µl) of the positive control was diluted to 100 µl with 0.076M phosphate buffered saline pH 6.4 (PBS), and the resulting dilutions were used as sample solutions. A 25 µl portion of the reaction solution of negative control was diluted with PBS and used for the measurement of background. Each sample was put in a glass vial to which 500 µg of streptavidin-sensitized magnetic particles (BioMag$^R$ Streptavidin, Advanced Magnetics) were subsequently added. After 1 hour of stirring at 37° C., 500 µl of PBS was added to the mixture, and the magnetic particles were separated from the supernatant using a magnetic separation apparatus (Ciba Corning). The thus collected particles were treated for dried at 100° C. for 5 minutes. Thereafter, 50 µl of each of 0.3M MGA dissolved in i-PrOH and of 1.2M hydrochloric acid in i-PrOH were added to the dried particles, and the mixture was sealed and heated at 100° C. for 1.5 hours. A 10 µl portion of each of the thus obtained reaction solutions was mixed with 400 μl of 2 mM L-cysteine/DMF solution, and the resulting luminescent intensity was measured in accordance with the procedure described in Example 9.

Figure 15:
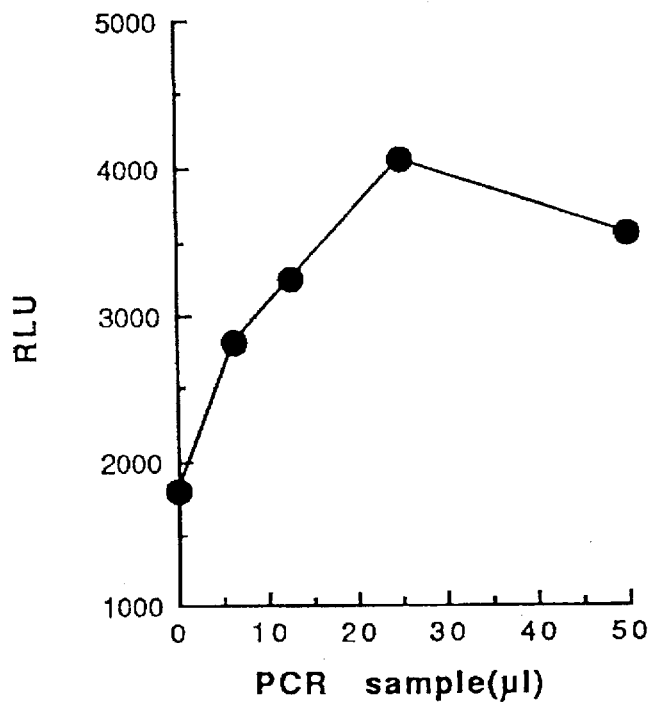
FIG. 15 is a graph showing a relationship between the amount of an amplified product prepared by PCR and the intensity of chemiluminescence when dUTP-biotin is used.
Figure 17:
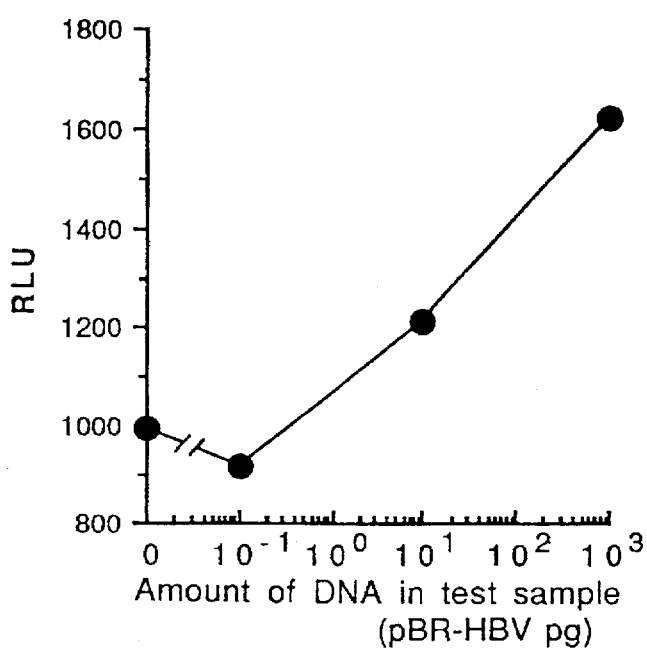
FIG. 17 is a graph showing a relationship between the concentration of an amplified product prepared by PCR and the intensity of luminescence when a centrifugation tube equipped with a filter for DNA recovery is used.
Figure 16:
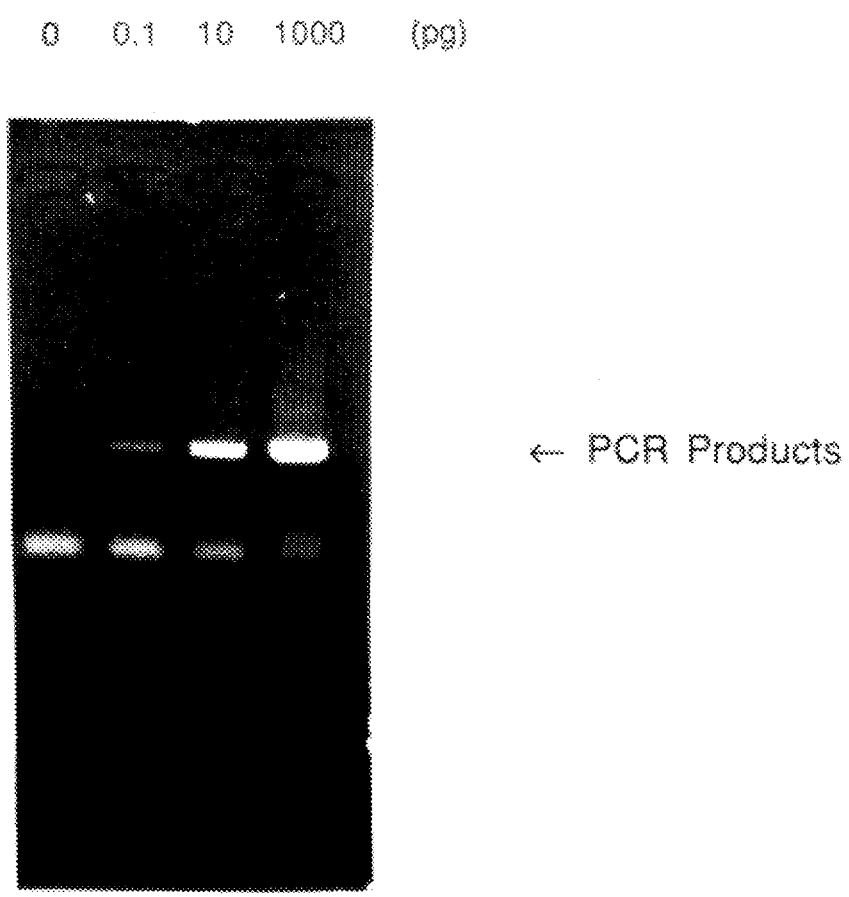
FIG. 16 is a picture showing results of electrophoresis.

The luminescent intensity increased in proportion to the amount of the PCR reaction solution (FIG. 15).

ii) A method applying a centrifugation tube equipped with a filter for DNA recovery Using B1 and B5R (amplification length, 850 bp) as primers and 0, 0.1, 10 and 1,000 pg of the pBR-HBV obtained in Example 7-1 as test samples, PCR was carried out under the same conditions described in Example 9. A 100 μl portion of each of the thus obtained reaction solutions was centrifuged at 6,400 rpm for 10 minutes using a centrifugation tube equipped with a filter for DNA recovery (SUPREC™-02, Takara Shuzo) which has been washed in advance with 400 μl of i-PrOH, and the resulting tube was washed by adding 100 μl of i-PrOH and centrifuging again at 6,400 rpm for 10 minutes. Next, 20 μl of distilled water was put on the filter of the tube to dissolve the thus recovered PCR amplification product. A 2 μl portion of each of the PCR amplification product solutions was subjected to electrophoresis using 1% agarose gel containing 0.5 μg/ml of ethidium bromide to confirm band of the amplified product (FIG. 16). The amplified product was recovered in proportion to the amount of test samples. A 10 μl portion of each of the amplified product-containing solutions was mixed with 90 μl of i-PrOH and allowed to react with 0.3M MGA in accordance with the protocol of Example 9 to measure luminescent intensity. As the results, the luminescent intensity increased in proportion to the amount of test samples (FIG. 17).

Thus, it is evident that qualitative or quantitative measurement of adenyl group-containing substances can be made by the use of the measuring method of the present invention simply and easily with high specificity and sensitivity and also with high S/N ratio.

What is claimed is:

1. A method for measuring an adenyl group-containing substance which comprises:

(i) deriving a chemiluminescent substance by reacting a compound represented by the following formula 1 with an adenyl group in the substance to be measured, in the presence of an acid catalyst;

$$R^1\text{---}CO\text{---}R^2 \quad (1)$$

wherein $R^1$ is a hydrogen atom, an alkyl group having 1 to 12 carbon atoms, an alkenyl group having 1 to 12 carbon atoms, an alkynyl group having 1 to 12 carbon atoms, an aryl group having 1 to 18 carbon atoms or an aromatic heterocyclic group having 1 to 18 carbon atoms;

wherein said $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and the group itself which substitutes or ring-condenses the $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group;

and wherein $R^2$ is an aldehyde group or a group represented by $-\text{CH}(OR^3)(OR^4)$ in which $R^3$ and $R^4$ are the same or different groups which may form a ring by their partial binding and are selected from a hydrogen atom, an alkyl group having 1 to 12 carbon atoms, an alkenyl group having 1 to 12 carbon atoms, an alkynyl group having 1 to 12 carbon atoms, and an aryl group having 1 to 18 carbon atoms;

wherein said $R^3$ and $R^4$ can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and the group itself which substitutes or ring-condenses the $R^3$ and $R^4$ groups can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group;

and (ii) qualitatively or quantitatively measuring said substance to be measured using luminescent intensity obtained from said chemiluminescent substance as an index.

2. The method of claim 1, wherein said adenyl group-containing substance is adenine, adenosine, an adenosine phosphate compound, DNA containing at least one adenine moiety or RNA containing at least one adenine moiety.

3. The method of claim 1, which further comprises a step (ia) of contacting the chemiluminescent substance derived in step (i) with a hydroxide solution initiator.

4. The method of claim 3, wherein said hydroxide solution is a sodium hydroxide solution.

5. The method of claim 3, wherein said contacting step (ia) is performed in a polar solvent selected from the group consisting of dimethylformamide, isopropanol, acetonitrile, dioxane, dimethylsulfoxide and water.

6. The method of claim 1, wherein $R^1$ is a phenyl group.

7. The method of claim 6, which further comprises a step (ia) of contacting the chemiluminescent substance derived in step (i) with a hydroxide solution initiator.

8. The method of claim 7, wherein said hydroxide solution is a sodium hydroxide solution.

9. The method of claim 8, wherein said contacting step (ia) is performed in a polar solvent selected from the group consisting of dimethylformamide, isopropanol, acetonitrile, dioxane, dimethyl sulfoxide and water.

10. The method of claim 1, wherein $R^1$ is an alkyl group.

11. The method of claim 10, which further comprises a step (ia) of contacting the chemiluminescent substance derived in step (i) with a hydroxide solution initiator.

12. The method of claim 11, wherein said hydroxide solution sodium hydroxide solution.

13. The method of claim 12, wherein said contacting step (ia) is performed in a polar solvent selected from the group consisting of dimethylformamide, isopropanol, acetonitrile, dioxane, dimethyl sulfoxide and water.

14. A method for measuring an adenyl group-containing substance in a target nucleic acid in a test sample using a capture probe which is complementary to the target nucleic acid, comprising:

i) hybridizing the capture probe with the target nucleic acid;

ii) reacting a compound of the formula 1

$$R^1\text{—CO—}R^2 \qquad (1)$$

with an adenyl group in the hybridized target nucleic acid obtained in step 1, in the presence of an acid catalyst, to obtain a chemiluminescent substance;

iii) qualitatively or quantitatively measuring the target nucleic acid by using a luminescent intensity of said chemiluminescent substance as an index; wherein:

$R^1$ is a hydrogen atom, an alkyl group having 1 to 12 carbon atoms, an alkenyl group having 1 to 12 carbon atoms, an alkynyl group having 1 to 12 carbon atoms, an aryl group having 1 to 18 carbon atoms or an aromatic heterocyclic group having 1 to 18 carbon atoms;

wherein said $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and the group itself which substitutes or ring-condenses the $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and wherein $R^2$ is an aldehyde group or a group represented by —CH(OR$^3$)(OR$^4$) in which $R^3$ and $R^4$ are the same or different groups which may form a ring by their partial binding and are selected from a hydrogen atom, an alkyl group having 1 to 12 carbon atoms, an alkenyl group having 1 to 12 carbon atoms, an alkynyl group having 1 to 12 carbon atoms, and an aryl group having 1 to 18 carbon atoms;

wherein said $R^3$ and $R^4$ can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and the group itself which substitutes or ring-condenses the $R^3$ and $R^4$ groups can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group.

15. The method of claim 14, wherein said target nucleic acid is first amplified by a polymerase chain reaction.

16. The method of claim 14, which further comprises a step (iia) of contacting the chemiluminescent substance obtained in step (ii) with a hydroxide solution initiator.

17. The method of claim 14, wherein said contacting step (iia) is performed in a polar solvent selected from the group consisting of dimethylformamide, isopropanol, acetonitrile, dioxane, dimethyl sulfoxide and water.

18. A method for measuring an adenyl group-containing substance in a target nucleic acid comprising the steps of:
   i) amplifying the target nucleic acid by polymerase chain reaction,
   ii) reacting the compound of the formula 1

   $$R^1\text{—CO—}R^2 \qquad (1)$$

with the adenyl group in the target nucleic acid amplified in step (i) to derive a chemiluminescent substance,
   (iii) qualitatively or quantitatively measuring the target nucleic acid by using a luminescent intensity of said chemiluminescent substance as an index wherein:
      $R^1$ is a hydrogen atom, an alkyl group having 1 to 12 carbon atoms, an alkenyl group having 1 to 12 carbon atoms, an alkynyl group having 1 to 12 carbon atoms, an aryl group having 1 to 18 carbon atoms or an aromatic heterocyclic group having 1 to 18 carbon atoms;
      wherein said $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and
      the group itself which substitutes or ring-condenses the $R^1$ may be substituted or ring-condensed with at least one group selected from the group consisting of a carboxyl group, hydroxyl group, amino group, amide group, sulfonamide group, sulfide group, sulfoxide group, sulfone group, nitro group; a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and wherein
      $R^2$ is an aldehyde group or a group represented by —CH(OR$^3$)(OR$^4$) in which $R^3$ and $R^4$ are the same or different groups which may form a ring by their partial binding and are selected from a hydrogen atom, an alkyl group having 1 to 12 carbon atoms, an alkenyl group having 1 to 12 carbon atoms, an alkynyl group having 1 to 12 carbon atoms, and an aryl group having 1 to 18 carbon atoms;
      wherein said $R^3$ and $R^4$ can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and
      the group itself which substitutes or ring-condenses the $R^3$ and $R^4$ groups can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group.

19. The method of claim 18, which further comprises a step (iia) of contacting the chemiluminescent substance obtained in step (i) with a hydroxide solution initiator.

20. The method of claim 18, wherein said contacting step (iia) is performed in a polar solvent selected from the group consisting of dimethylformamide, isopropanol, acetonitrile, dioxane, dimethyl sulfoxide and water.

21. A method for detecting or quantitating a substance in a test sample comprising:
   i) labeling an antigen or antibody with an adenyl group-containing substance or a nucleic acid containing adenine to obtain an adenine-labelled antigen or antibody;
   ii) reacting the adenine-labelled antigen or antibody obtained in step (i) with the substance to be measured, to form an adenine-labelled complex;
   iii) reacting a compound of the formula 1

   $$R^1\text{—CO—}R^2 \qquad (1)$$

with the adenine-labeled complex obtained in step (ii), in the presence of an acid catalyst, to derive a chemiluminescent substance, wherein;
      $R^1$ is a hydrogen atom, an alkyl group having 1 to 12 carbon atoms, an alkenyl group having 1 to 12 carbon atoms, an alkynyl group having 1 to 12 carbon atoms, an aryl group having 1 to 18 carbon atoms or an aromatic heterocyclic group having 1 to 18 carbon atoms;
      wherein said $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and
      the group itself which substitutes or ring-condenses the $R^1$ may be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and wherein $R^2$ is an aldehyde group or a group represented by —CH(OR$^3$)(OR$^4$) in which $R^3$ and $R^4$ are the same or different groups which may form a ring by their partial binding and are selected from a hydrogen atom, an alkyl group having 1 to 12 carbon atoms, an alkenyl group having 1 to 12 carbon atoms, an alkynyl group having 1 to 12 carbon atoms, and an aryl group having 1 to 18 carbon atoms;

wherein said $R^3$ and $R^4$ can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group; and the group itself which substitutes or ring-condenses the $R^3$ and $R^4$ groups can be substituted or ring-condensed with at least one group selected from the group consisting of a carboxyl group, hydroxyl group, amino group, amide group, sulfonamide group, sulfide group, sulfoxide group, sulfone group, nitro group, a halide atom, mercapto group, carbonyl group, azide group, an alkylamino group having 1 to 12 carbon atoms, an alkyl group having 1 to 12 carbon atoms, an alkenyl group having 1 to 12 carbon atoms, an alkynyl group having 1 to 12 carbon atoms, an alkoxy group having 1 to 12 carbon atoms, a polyalkoxy group, an aryl group, an aryloxy group, and a heterocyclic group;

and iv) qualitatively or quantitatively measuring the substance to be measured by a luminescent intensity from the chemiluminescent substance obtained in step (iii) as an index.

22. The method of claim 21, wherein said adenine-containing labelling substance is a nucleic acid and further comprising a step (iia) in which said nucleic acid is amplified by a polymerase chain reaction.

23. The method of claim 21, which further comprises a step (iiia) of contacting said chemilumiscent substance obtained in step (iii) with a hydroxide solution initiator.

24. The method of claim 21, wherein said contacting step (iiia) is performed in a polar solvent selected from the group consisting of dimethylformamide, isopropanol, acetonitrile, dioxane, dimethyl sulfoxide and water.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i x ) FEATURE:
        ( A ) NAME/KEY: -
        ( B ) LOCATION: 1..30
        ( D ) OTHER INFORMATION: /label=oligonucleotide
            / note="B1 PCR primer"

( x i ) SEQUENCE DESCRIPTION: SEQ ID NO:1:

TTTTTTTTT CTCTGCCTAA TCATCTCATG        30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: YES ( i x ) FEATURE:
        ( A ) NAME/KEY: -
        ( B ) LOCATION: 1..30
        ( D ) OTHER INFORMATION: /label=oligonucleotide
            / note="B2R PCR primer"

( x i ) SEQUENCE DESCRIPTION: SEQ ID NO:2:

TTTTTTTTT CAAATTCTTT ATACGGGTCA        30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..30
        ( D ) OTHER INFORMATION: /label=oligonucleotide
            / note="B3R PCR primer"

( x i ) SEQUENCE DESCRIPTION: SEQ ID NO:3:

TTTTTTTTT TCTAAGGCCT CCCGATATAG      30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..30
        ( D ) OTHER INFORMATION: /label=oligonucleotide
            / note="B4R PCR primer"

( x i ) SEQUENCE DESCRIPTION: SEQ ID NO:4:

TTTTTTTTT AAGTAAGACA GGAAATGTGA      30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( i v ) ANTI-SENSE: YES ( i x ) FEATURE:
        ( A ) NAME/KEY: -
        ( B ) LOCATION: 1..30
        ( D ) OTHER INFORMATION: /label=oligonucleotide
            / note="B5R PCR primer"

( x i ) SEQUENCE DESCRIPTION: SEQ ID NO:5:

TTTTTTTTT TAGGATAGAA CCTAGCAGGC      30

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

-continued

```
( i v ) ANTI-SENSE: NO ( i x ) FEATURE:
        ( A ) NAME/KEY: -
        ( B ) LOCATION: 1..20
        ( D ) OTHER INFORMATION: /label=oligonucleotide
                / note="E0001 PCR primer"

( x i ) SEQUENCE DESCRIPTION: SEQ ID NO:6:

AAATTGAAGA GTTTGATCAT                                                    20

( 2 ) INFORMATION FOR SEQ ID NO:7:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: DNA (synthetic)

( i v ) ANTI-SENSE: YES ( i x ) FEATURE:
                ( A ) NAME/KEY: -
                ( B ) LOCATION: 1..20
                ( D ) OTHER INFORMATION: /label=oligonucleotide
                        / note="E1000R PCR primer"

( x i ) SEQUENCE DESCRIPTION: SEQ ID NO:7:

TGGATGTCAA GACCAGGTAA                                                    20
```